(12) United States Patent
Schallner et al.

(10) Patent No.: US 6,677,277 B1
(45) Date of Patent: Jan. 13, 2004

(54) SUBSTITUTED SULPHONYL AMINO(THIO) CARBONYL COMPOUNDS AND THEIR USE AS HERBICIDES

(75) Inventors: Otto Schallner, Monheim (DE); Mark-Wilhelm Drewes, Langenfeld (DE); Kurt Findeisen, Leverkusen (DE); Ernst-Rudolf F. Gesing, Erkrath (DE); Johannes-Rudolf Jansen, Monheim (DE); Rolf Kirsten, Monheim (DE); Joachim Kluth, Langenfeld (DE); Klaus-Helmut Müller, Düsseldorf (DE); Klaus König, Odenthal (DE); Ulrich Philipp, Köln (DE); Hans-Jochem Riebel, Wuppertal (DE); Peter Wolfrum, Langenfeld (DE); Markus Dollinger, Overland Park, KS (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/194,261
(22) PCT Filed: May 16, 1997
(86) PCT No.: PCT/EP97/02520
§ 371 (c)(1), (2), (4) Date: May 13, 1999
(87) PCT Pub. No.: WO97/46540
PCT Pub. Date: Dec. 11, 1997

(30) Foreign Application Priority Data

May 30, 1996 (DE) .......................... 196 21 685

(51) Int. Cl.[7] .......................... A01N 47/38; C07D 249/12
(52) U.S. Cl. ................. 504/139; 548/263.2; 548/263.4; 548/263.8
(58) Field of Search ............... 548/263.2, 263.4, 548/263.8; 504/139

(56) References Cited

U.S. PATENT DOCUMENTS

| | | | |
|---|---|---|---|
| 4,310,346 A | 1/1982 | Levitt et al. | ................... 23/92 |
| 4,645,527 A | 2/1987 | Amuti et al. | ................... 71/90 |
| 5,057,144 A | * 10/1991 | Daum et al. | ................... 504/273 |
| 5,085,684 A | 2/1992 | Muller et al. | ................ 422/341 |
| 5,094,683 A | 3/1992 | Daum et al. | ................ 341/422 |
| 5,149,356 A | 9/1992 | Muller et al. | ................ 341/422 |
| 5,205,853 A | 4/1993 | Wolf et al. | ................. 459/247 |
| 5,238,910 A | 8/1993 | Muller et al. | ............... 422/425 |
| 5,241,074 A | 8/1993 | Daum et al. | ................ 341/422 |
| 5,252,540 A | 10/1993 | Heistracher et al. | ........... 4/280 |
| 5,256,632 A | 10/1993 | Wolf et al. | ................. 459/569 |
| 5,597,939 A | 1/1997 | M uller et al. | ................. 507/8 |
| 5,599,944 A | 2/1997 | M uller et al. | ............. 422/431 |
| 5,625,074 A | 4/1997 | Daum et al. | ............. 341/263.8 |
| 5,631,380 A | 5/1997 | Haas et al. | ................. 341/534 |
| 5,652,372 A | 7/1997 | Muller et al. | ................ 422/341 |
| 5,750,718 A | 5/1998 | Muller et al. | ............. 425/263.6 |

FOREIGN PATENT DOCUMENTS

| | | |
|---|---|---|
| DE | 3624103 | 6/1996 |
| WO | 95/27703 | 10/1995 |
| WO | 96/11188 | 4/1996 |

OTHER PUBLICATIONS

Database Crossfire, pp. 1277–1289, vol. 90, (month unavailable)1960, Gazz. Chim. Ital.
Collection of Czechoslovak Chemical Communications, vol. 47, Mar. 29, 1982 , pp. 72–87 K. Sindelar et al.
Database Crossfire, J. Chem. Soc., vol. 73, (month unavailable) 1898, p. 751–777 (See p. 753).

* cited by examiner

Primary Examiner—Joseph K. McKane
Assistant Examiner—Kamal Saeed
(74) Attorney, Agent, or Firm—Richard E. L. Henderson; Raymond J. Harmuth; John E. Mrozinski. Jr.

(57) ABSTRACT

The invention relates to novel sulfonylamino(thio)carbonyl compounds of the formula (I),

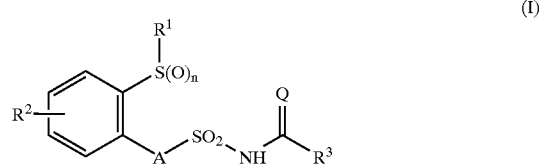

(I)

in which
n represents the numbers 0, 1 or 2,
A represents a single bond, or oxygen or sulfur, or the grouping N—R, in which R represents hydrogen, alkyl, alkenyl, alkinyl or cycloalkyl,
Q represents oxygen or sulfur,
$R^1$ represents hydrogen or formyl, or represents respectively optionally substituted alkyl, alkoxy, alkylamino, alkoxyamino, dialkylamino, N-alkoxy-N-alkyl-amino, alkylcarbonyl, alkoxycarbonyl, alkylsulfonyl, alkenyl, alkinyl, cycloalkyl, cycloalkylcarbonyl or cycloalkylsulfonyl,
$R^2$ represents cyano or halogen, or represents respectively optionally substituted alkyl, alkoxy, alkylthio, alkylsulfinyl, alkylsulfonyl, dialkylaminosulfonyl, alkenyl, alkinyl, alkenyloxy or alkinyloxy, and
$R^3$ represents respectively optionally substituted heterocyclyl having 5 ring members of which at least one is oxygen, sulfur or nitrogen and from one to three further ring members can be nitrogen,
and salts of compounds of the formula (I), a plurality of processes and novel intermediates for preparing them and their use as herbicides.

8 Claims, No Drawings

SUBSTITUTED SULPHONYL AMINO(THIO) CARBONYL COMPOUNDS AND THEIR USE AS HERBICIDES

This application is a 371 of International Application PCT/EP97/02520 filed May 16, 1997.

TECHNICAL FIELD OF THE INVENTION

The invention relates to novel substituted sulfonylamino(thio)carbonyl compounds, to a plurality of processes and to novel intermediates for preparing them, and to their use as herbicides.

BACKGROUND OF THE INVENTION

It is already known that certain sulfonylaminocarbonyl compounds have herbicidal properties (cf. EP 341489, EP 422469, EP 425948, EP 431291, EP 507171, EP 534266, DE 4029753). The action of these compounds, however, is not satisfactory in every respect.

DETAILED DESCRIPTION OF THE INVENTION

This invention, then, provides the novel sulfonylamino(thio)carbonyl compounds of the general formula (I)

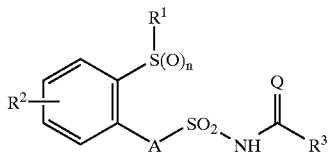

(I)

in which n represents the numbers 0, 1 or 2,

A represents a single bond, or oxygen or sulfur, or the grouping N—R, in which R represents hydrogen, alkyl, alkenyl, alkinyl or cycloalkyl, Q represents oxygen or sulfur, $R^1$ represents hydrogen or formyl or represents respectively optionally substituted alkyl, alkoxy, alkylamino, alkoxyamino, dialkylamino, N-alkoxy-N-alkyl-amino, alkylcarbonyl, alkoxycarbonyl, alkylsulfonyl, alkenyl, alkinyl, cycloalkyl, cycloalkylcarbonyl or cycloalkylsulfonyl, $R^2$ represents cyano or halogen or represents respectively optionally substituted alkyl, alkoxy, alkylthio, alkylsulfinyl, alkylsulfonyl, dialkylaminosulfonyl, alkenyl, alkinyl, alkenyloxy or alkinyloxy, and $R^3$ represents respectively optionally substituted heterocyclyl having 5 ring members of which at least one is oxygen, sulfur or nitrogen and from one to three further ring members can be nitrogen, and salts of compounds of the formula (I).

The novel substituted sulfonylamino(thio)carbonyl compounds of the general formula (I) are obtained by reacting (a) aminosulfonyl compounds of the general formula (II)

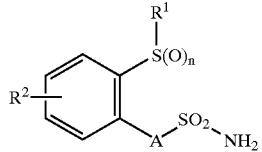

(II)

in which n, A, $R^1$ and $R^2$ are each as defined above with (thio)carboxylic acid derivatives of the general formula (III)

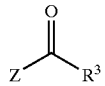

(III)

in which

Q and $R^3$ are each as defined above and

Z represents halogen, alkoxy, aryloxy or arylalkoxy, optionally in the presence of an acid acceptor and optionally in the presence of a diluent, or (b) sulfonyl iso(thio)cyanates of the general formula (IV)

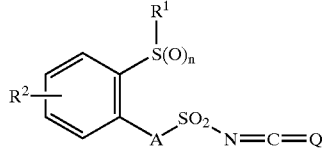

(IV)

in which n, A, Q, $R^1$ and $R^2$ are each as defined above with heterocycles of the general formula (V)

$$H—R^3 \quad (V)$$

in which $R^3$ is as defined above, optionally in the presence of a reaction auxiliary and optionally in the presence of a diluent, or (c) chlorosulfonyl compounds of the general formula (VI)

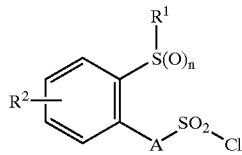

(VI)

in which n, A, $R^1$ and $R^2$ are each as defined above with heterocycles of the general formula (V)

$$H—R^3 \quad (V)$$

in which $R^3$ is as defined above and metal (thio)cyanates of the general formula (VII)

$$MQCN \quad (VII)$$

in which

Q is as defined above, optionally in the presence of a reaction auxiliary and optionally in the presence of a diluent, or (d) chlorosulfonyl compounds of the general formula (VI)

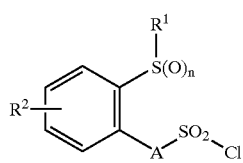
(VI)

in which n, A, $R^1$ and $R^2$ are each as defined above, with (thio)carboxamides of the general formula (VIII)

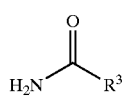
(VIII)

in which

Q and $R^3$ are each as defined above, optionally in the presence of an acid acceptor and optionally in the presence of a diluent, or (e) sulfonylamino(thio)carbonyl compounds of the general formula (IX)

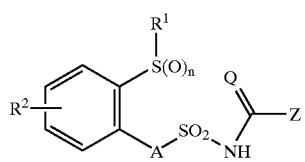
(IX)

in which n, A, Q, $R^1$ and $R^2$ are each as defined above and

Z represents halogen, alkoxy, aryloxy or arylalkoxy, with heterocycles of the general formula (V)

(V)

in which $R^3$ is as defined above, optionally in the presence of an acid acceptor and optionally in the presence of a diluent, or (f) heterocycles of the general formula (V)

(V)

in which $R^3$ is as defined above, with chlorosulfonyl iso(thio)cyanate, optionally in the presence of a diluent, and reacting the adducts formed in this reaction in situ with benzene derivatives of the general formula (X)

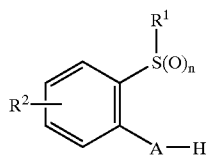
(X)

in which n, A, $R^1$ and $R^2$ are each as defined above, optionally in the presence of an acid acceptor and optionally in the presence of a diluent, and converting, if desired, the compounds of the formula (I) obtained by processes (a), (b), (c), (d), (e) or (f) by customary methods into salts.

The novel substituted sulfonylamino(thio)carbonyl compounds of the general formula (I) have strong herbicidal activity.

The invention preferably provides compounds of the formula (I) in which n represents the numbers 0, 1 or 2, A represents a single bond, or oxygen or sulfur, or the grouping N—R, in which R represents hydrogen, $C_1$–$C_6$-alkyl, $C_2$–$C_6$-alkenyl, $C_2$–$C_6$-alkinyl or $C_3$–$C_6$-cycloalkyl, Q represents oxygen or sulfur, $R^1$ represents hydrogen or formyl or represents respectively optionally cyano-, fluoro-, chloro-, bromo-, phenyl- or $C_1$–$C_4$-alkoxy-substituted alkyl, alkoxy, alkylamino, alkoxyamino, dialkylamino, N-alkoxy-N-alkyl-amino, alkylcarbonyl, alkoxycarbonyl, alkylsulfonyl, alkenyl or alkinyl having in each case up to 6 carbon atoms, or represents respectively optionally cyano-, fluoro-, chloro-, bromo- or $C_1$–$C_4$-alkyl-substituted $C_3$–$C_6$-cycloalkyl, $C_3$–$C_6$-cycloalkyl-carbonyl or $C_3$–$C_6$-cycloalkyl-sulfonyl, $R^2$ represents cyano, fluoro, chloro or bromo or represents respectively optionally cyano-, fluoro-, chloro-, bromo- or $C_1$–$C_4$-alkoxy-substituted alkyl, alkoxy, alkylthio, alkylsulfinyl, alkylsulfonyl, dialkylaminosulfonyl, alkenyl, alkinyl, alkenyloxy or alkinyloxy having in each case up to 6 carbon atoms, and $R^3$ represents respectively optionally substituted heterocyclyl of the formulae below,

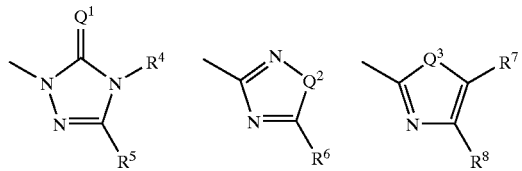

in which $Q^1$, $Q^2$ and $Q^3$ each represent oxygen or sulfur, and $R^4$ represents hydrogen, hydroxyl, amino or cyano, or represents $C_2$–$C_{10}$-alkylideneamino, or represents optionally fluoro-, chloro-, bromo-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, or represents respectively optionally fluoro-, chloro- and/or bromo-substituted $C_2$–$C_6$-alkenyl or $C_2$–$C_6$-alkinyl, or represents respectively optionally fluoro-, chloro-, bromo-, cyano-, $C_1$–$C_4$-alkoxy- or $C_1$–$C_4$-alkoxy-carbonyl-substituted $C_1$–$C_6$-alkoxy, $C_1$–$C_6$- alkylamino or $C_1$–$C_6$-alkyl-carbonylamino, or represents $C_3$–$C_6$-alkenyloxy, or represents di-($C_1$–$C_4$-alkyl)-amino, or represents respectively optionally fluoro-, chloro-, bromo-, cyano- and/or $C_1$–$C_4$-alkyl-substituted $C_3$–$C_6$-cycloalkyl, $C_3$–$C_6$-cycloalkylamino or $C_3$–$C_6$-cycloalkyl-$C_1$–$C_4$-alkyl, or represents respectively optionally fluoro-, chloro-, bromo-, cyano-, nitro-, $C_1$–$C_4$-alkyl-, trifluoromethyl- and/or $C_1$–$C_4$-alkoxy-substituted phenyl or phenyl-$C_1$–$C_4$-alkyl, $R^5$ represents hydrogen, hydroxyl, mercapto, amino, cyano, fluoro, chloro, bromo or iodo, or represents optionally fluoro-, chloro-, bromo-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, or represents respectively optionally fluoro-, chloro- and/or bromo-substituted $C_2$–$C_6$-alkenyl or $C_2$–$C_6$-alkinyl, or represents respectively optionally fluoro-, chloro-, cyano-, $C_1$–$C_4$-alkoxy- or $C_1$–$C_4$-alkoxy-carbonyl-substituted $C_1$–$C_6$-alkoxy, $C_1$–$C_6$-alkylthio, $C_1$–$C_6$-alkylamino or $C_1$–$C_6$-alkylcarbonylamino, or represents $C_3$–$C_6$-alkenyloxy, $C_3$–$C_6$-alkinyloxy, $C_3$–$C_6$-alkenylthio, $C_3$–$C_6$-alkinylthio, $C_3$–$C_6$-alkenylamino or $C_3$–$C_6$-alkinylamino, or represents di-($C_1$–$C_4$-alkyl)-amino, or represents respectively optionally methyl- and/or ethyl-substituted aziridino, pyrrolidino, piperidino or morpholino, or represents respectively optionally fluoro-, chloro-, bromo-, cyano- and/or $C_1$–$C_4$-alkyl-substituted $C_3$–$C_6$-cycloalkyl, $C_5$–$C_6$-cycloalkenyl, $C_3$–$C_6$-cycloalkyloxy, $C_3$–$C_6$-cycloalkylthio, $C_3$–$C_6$-cycloalkylamino, $C_3$–$C_6$-cycloalkyl-$C_1$–$C_4$-alkyl, $C_3$–$C_6$-cycloalkyl-$C_1$–$C_4$-alkoxy, $C_3$–$C_6$-cycloalkyl-$C_1$–$C_4$-alkylthio or $C_3$–$C_6$-cycloalkyl-$C_1$–$C_4$-alkylamino, or represents respectively optionally fluoro-, chloro-, bromo-, cyano-, nitro-, $C_1$–$C_4$-alkyl-, trifluoromethyl-, $C_1$–$C_4$-alkoxy- and/or $C_1$–$C_4$-alkoxy-carbonyl-substituted phenyl, phenyl-$C_1$–$C_4$-alkyl, phenoxy, phenyl-$C_1$–$C_4$-alkoxy, phenylthio, phenyl-$C_1$–$C_4$-alkylthio, phenylamino or phenyl-$C_1$–$C_4$-alkylamino, or $R^4$ and $R^5$ together represent optionally branched alkanediyl having 3 to 11 carbon atoms, and $R^6$, $R^7$ and $R^8$ are identical or different and each represent hydrogen, cyano, fluoro, chloro, bromo, or represent respectively optionally fluoro-, chloro-, bromo- or $C_1$–$C_4$-alkoxy-substituted alkyl, alkenyl, alkinyl, alkoxy, alkenyloxy, alkinyloxy, alkylthio, alkenylthio, alkinylthio, alkylsulfinyl or alkylsulfonyl having in each case up to 6 carbon atoms, or represent optionally cyano-, fluoro-, chloro-, bromo- or $C_1$–$C_4$-alkyl-substituted cycloalkyl having 3 to 6 carbon atoms.

The invention further preferably provides the sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulfonium, $C_5$- or $C_6$-cycoalkyl-ammonium and di-($C_1$–$C_2$-alkyl)-benzyl-ammonium salts of compounds of the formula (I) in which n, A, Q, $R^1$, $R^2$ and $R^3$ each have the meanings indicated. above as preferred.

The invention relates in particular to compounds of the formula (I) in which n represents the numbers 0, 1 or 2, A represents a single bond, or oxygen or the grouping N—R, in which R represents hydrogen, methyl, ethyl, n- or i-propyl, n-, i- or s-butyl, propenyl, butenyl, propinyl, butinyl, cyclopropyl, cyclobutyl, cyclopentyl or cyclohexyl, Q represents oxygen or sulfur, $R^1$ represents hydrogen or formyl, or represents respectively optionally fluoro-, chloro-, bromo-, methoxy- or ethoxy-substituted methyl, ethyl, n- or i-propyl, n-, i- or s-butyl, methoxy, ethoxy, n- or i-propoxy, n-, i-, s- or t-butoxy, methylamino, ethylamino, n- or i-propylamino, n-, i-, s- or t-butylamino, methoxyamino, ethoxyamino, n- or i-propoxyamino, n-, i-, s- or t-butoxyamino, dimethylamino, diethylamino, N-methoxy-N-methyl-amino, acetyl, propionyl, butyroyl, methoxycarbonyl, ethoxycarbonyl, n- or i-propoxycarbonyl, methylsulfonyl, ethylsulfonyl, n- or i-propylsulfonyl, n-, i-, s- or t-butylsulfonyl, propenyl, butenyl, propinyl or butinyl, or represents respectively optionally fluoro-, chloro- or methyl-substituted cyclopropyl, cyclopropylcarbonyl or cyclopropylsulfonyl, $R^2$ represents cyano, fluoro, chloro or bromo, or represents respectively optionally fluoro-, chloro-, methoxy- or ethoxy-substituted methyl, ethyl, n- or i-propyl, n-, i- or s-butyl, methoxy, ethoxy, n- or i-propoxy, n-, i- or s-butoxy, methylthio, ethylthio, n- or i-propylthio, n-, i-, s- or t-butylthio, methylsulfinyl, ethylsulfinyl, methylsulfonyl, ethylsulfonyl, dimethylaminosulfonyl or diethylaminosulfonyl, or represents propenyl, butenyl, propinyl, butinyl, propenyloxy, butenyloxy, propinyloxy or butinyloxy, and $R^3$ represents respectively optionally substituted heterocyclyl of the formulae below:

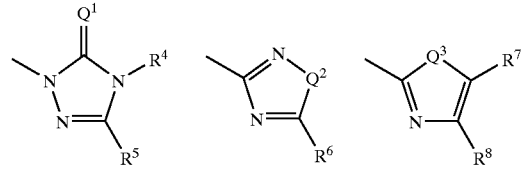

in which $Q^1$, $Q^2$ and $Q^3$ each represent oxygen or sulfur, and $R^4$ represents hydrogen, hydroxyl or amino, or represents $C_3$–$C_8$-alkylideneamino, or represents respectively optionally fluoro-, chloro-, cyano-, methoxy- or ethoxy-substituted methyl, ethyl, n- or i-propyl, n-, i-, s- or t-butyl, or represents respectively optionally fluoro-, chloro- or bromo-substituted propenyl, butenyl, propinyl or butinyl, or represents respectively optionally fluoro-, chloro-, cyano-, methoxy- or ethoxy-substituted methoxy, ethoxy, n- or i-propoxy, n-, i-, s- or t-butoxy, methylamino, ethylamino, n- or i-propylamino, n-, i-, s- or t-butylamino, or represents propenyloxy or butenyloxy, or represents dimethylamino or diethylamino, or represents respectively optionally fluoro-, chloro-, methyl- and/or ethyl-substituted cyclopropyl, cyclobutyl, cyclopentyl, cyclohexyl, cyclopropylamino, cyclobutylamino, cyclopentylamino, cyclohexylamino, cyclopropylmethyl, cyclobutylmethyl, cyclopentylmethyl or cyclohexylmethyl, or represents respectively optionally fluoro-, chloro-, methyl-, trifluoromethyl- and/or methoxy-substituted phenyl or benzyl, $R^5$ represents hydrogen, hydroxyl, mercapto, amino, fluoro, chloro or bromo, or represents respectively optionally fluoro-, chloro-, cyano-, methoxy- or ethoxy-substituted methyl, ethyl, n- or i-propyl, n-, i-, s- or t-butyl, or represents respectively optionally fluoro-, chloro- or bromo-substituted ethenyl, propenyl, butenyl, propinyl or butinyl, or represents respectively optionally fluoro-, chloro-, cyano-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, or represents propenyloxy, butenyloxy, propinyloxy, butinyloxy, propenylthio, propadienylthio, butenylthio, propinylthio, butinylthio, propenylamino, butenylamino, propinylamino or butinylamino, or represents dimethylamino, diethylamino or dipropylamino, or represents respectively optionally fluoro-, chloro-, methyl- and/or ethyl-substituted cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents respectively optionally fluoro-, chloro-, methyl-, trifluoromethyl-, methoxy- and/or methoxycarbonyl-substituted phenyl, benzyl, phenoxy, benzyloxy, phenylthio, benzylthio, phenylamino or benzylamino, or $R^4$ and $R^5$ together represent optionally branched alkanediyl having 3 to 11 carbon atoms, furthermore $R^6$, $R^7$ and $R^8$ are identical or different and each represent hydrogen, cyano, fluoro, chloro or bromo, or represent respectively optionally fluoro-, chloro-, methoxy- or ethoxy-substituted methyl, ethyl, n- or i-propyl, n-, i-, s- or t-butyl, propenyl, butenyl, propinyl, butinyl, methoxy, ethoxy, n- or i-propoxy, n-, i-, s- or t-butoxy, propenyloxy, butenyloxy, propinyloy, butinyloxy, methylthio, ethylthio, n- or i-propylthio, n-, i-, s- or t-butylthio, propenylthio, butenylthio, propinylthio, butinylthio, methylsulfinyl, ethylsulfinyl, methylsulfonyl or ethylsulfonyl, or represent cyclopropyl.

A very particularly preferred group of compounds according to the invention are those compounds of the formula (I) in which n represents the numbers 0, 1 or 2, A represents a single bond, Q represents oxygen or sulfur, $R^1$ represents respectively optionally fluoro- and/or chloro-substituted methyl, ethyl, n- or i-propyl, n-, i-, s- or t-butyl, $R^2$ represents fluoro, chloro or bromo, or represents respectively optionally fluoro-, and/or chloro-substituted methyl, ethyl, methoxy, ethoxy, methylthio or ethylthio—in each case in position 6-, and $R^3$ represents optionally substituted triazolinyl of the formula below,

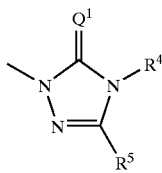

in which $Q^1$ represents oxygen or sulfur, and $R^4$ represents respectively optionally fluoro-, chloro-, cyano-, methoxy- or ethoxy-substituted methyl, ethyl, n- or i-propyl, or represents propenyl or propinyl, or represents methoxy, ethoxy, n- or i-propoxy, or represents cyclopropyl, and $R^5$ represents hydrogen, chloro or bromo, or represents respectively optionally fluoro-, chloro-, cyano-, methoxy- or ethoxy-substituted methyl, ethyl, n- or i-propyl, or represents respectively optionally fluoro- and/or chloro-substituted propenyl or propinyl, or represents respectively optionally fluoro-, chloro-, cyano-, methoxy- or ethoxy-substituted methoxy, ethoxy, n- or i-propoxy, methylthio, ethylthio, n- or i-propylthio, or represents propenyloxy or cyclopropyl.

Q represents oxygen or sulfur, $R^1$ represents respectively optionally fluoro- and/or chloro-substituted methyl, ethyl, n- or i-propyl, n-, i-, s- or t-butyl, $R^2$ represents fluoro, chloro or bromo, or represents respectively optionally fluoro- and/or chloro-substituted methyl, ethyl, methoxy, ethoxy, methylthio or ethylthio—in each case in position 6-, and $R^3$ represents optionally substituted triazolinyl of the formula below,

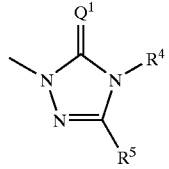

in which $Q^1$ represents oxygen or sulfur, and $R^4$ represents respectively optionally fluoro-, chloro-, cyano-, methoxy- or ethoxy-substituted methyl, ethyl, n- or i-propyl, or represents propenyl or propynyl, or represents methoxy, ethoxy, n- or i-propoxy, or represents cyclopropyl, and $R^5$ represents hydrogen, chloro or bromo, or represents respectively optionally fluoro-, chloro-, cyano-, methoxy- or ethoxy-substituted methyl, ethyl, n- or i-propyl, or represents respectively optionally fluoro- and/or chloro-substituted propenyl or propinyl, or represents respectively optionally fluoro-, chloro-, cyano-, methoxy- or ethoxy-substituted methoxy, ethoxy, n- or i-propoxy, methylthio, ethylthio, n- or i-propylthio, or represents propenyloxy or cyclopropyl.

The radical definitions listed above, whether general or listed in ranges of preference, apply not only to the end products of the formula (I) but also, correspondingly, to the starting materials and/or intermediates required in each case for the preparation. These radical definitions can be combined as desired with one another, thus including combinations between the preferred ranges indicated.

Using, for example, 2-fluoro-6-methylthio-benzenesulfonamide and 5-ethoxy4-methyl-2-phenoxycarbonyl-2,4-dihydro-3H-1,2,4-triazole-3-thione as starting materials, the course of reaction in the process (a) according to the invention can be illustrated by the following equation:

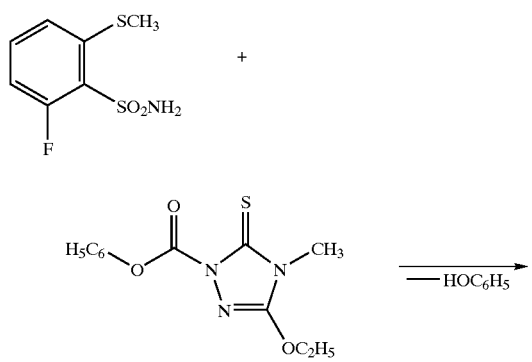

Using, for example, 2-ethylthio-6-methyl-phenylsulfonyl isothiocyanate and 5-ethyl-4-methoxy-2,4-dihydro-3H-1,2,4-triazol-3-one as starting materials, the course of reaction in the process (b) according to the invention can be illustrated by the following equation:

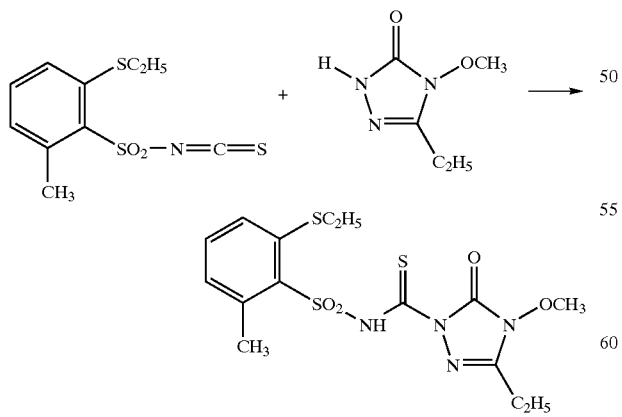

Using, for example, 2-methylthio-3-methyl-benzenesulfonyl chloride, 5-ethyl-thio-4-methoxy-2,4-dihydro-3H-1,2,4-triazol-3-one and potassium cyanate as starting materials, the course of reaction in the process (c) according to the invention can be illustrated by the following equation:

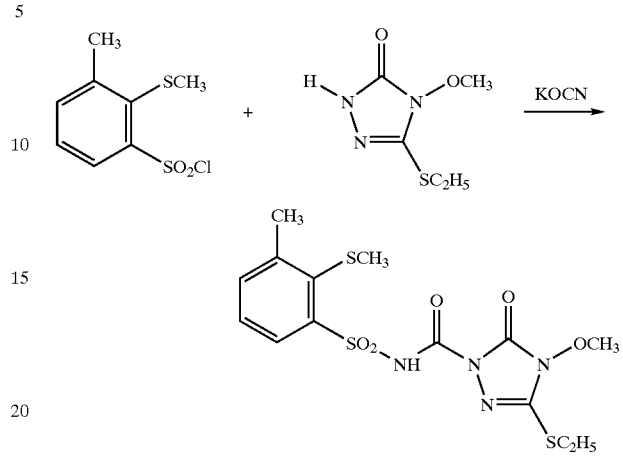

Using, for example, 2-ethylthio-4-fluoro-benzenesulfonyl chloride and 5-methyl-1,2,4-oxadiazole-3-carboxamide as starting materials, the course of reaction in the process (d) according to the invention can be illustrated by the following equation:

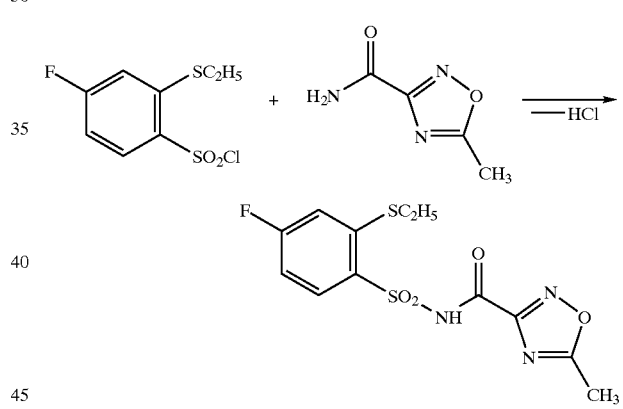

Using, for example, N-(2-chloro-6-propylthio-phenylsulfonyl)-O-methylurethane and 4-methyl-5-methylthio-2,4-dihydro-3H-1,2,4-triazol-3-one as starting materials, the course of reaction in the process (e) according to the invention can be illustrated by the following equation:

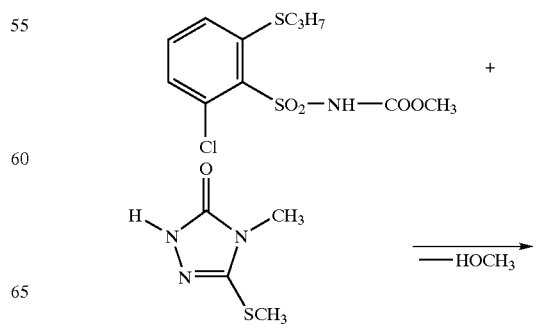

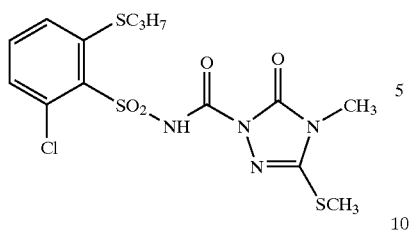

Using, for example, 5-chloro-4-ethyl-2,4-dihydro-3H-1,2,4-triazol-3-one and chlorosulfonyl isocyanate and then 2-ethylthio-6-methyl-aniline as starting materials, the course of reaction in the process (f) according to the invention can be illustrated by the following equation:

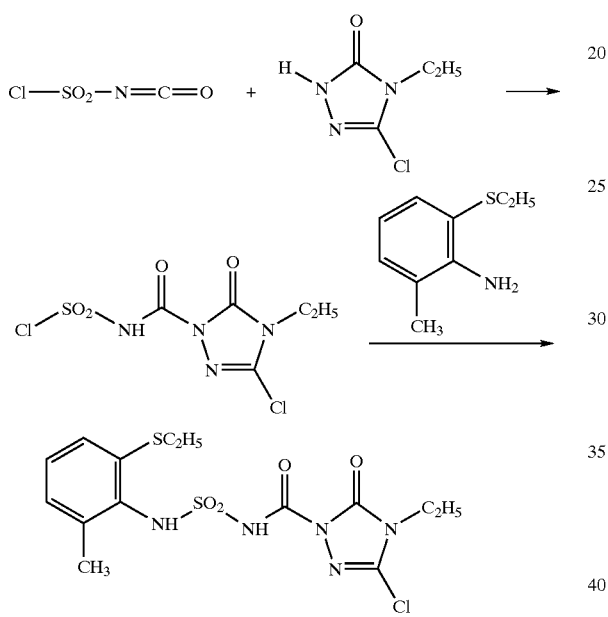

A general definition of the aminosulfonyl compounds to be used as starting materials in the process (a) according to the invention for the preparation of compounds of the formula (I) is given by the formula (II). In the formula (II), n, A, $R^1$ and $R^2$ preferably or in particular have that meaning which has already been indicated above, in connection with the description of the compounds of the formula (I) according to the invention, as being preferable or, respectively, particularly preferable for n, A, $R^1$ and $R^2$.

With the exception of the compound 2,6-bis-methylthio-benzenesulfonamide (cf. EP 135332, U.S. Pat. No. 4,604,131), the starting materials of the formula (II) have to date not been disclosed in the literature; with the exception of 2,6-bis-methylthio-benzenesulfonamide, they are novel substances and likewise form part of the subject matter of the present application.

The novel aminosulfonyl compounds of the formula (II) in which n represents zero, A represents a single bond and $R^1$ represents respectively optionally substituted alkyl, alkenyl, alkinyl or cycloalkyl are obtained when t-butylaminosulfonyl compounds of the general formula (XI)

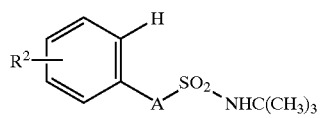

in which

A and $R^2$ are each as defined above are metallated—i.e. the hydrogen atom shown in the formula (XI) is replaced by a metal atom—with an organometallic compound, such as for example butyllithium in hexane, if appropriate in the presence of a (further) inert diluent, such as for example tetrahydrofuran, and under an inert gas atmosphere, such as for example under argon, at temperatures between −50° C. and +20° C., and then, in the same reaction medium, reacted with sulfur at temperatures between −30° C. and +30° C.—i.e. the metal atom is replaced by sulfur—, and then, in the same reaction medium, reacted with an alkylating agent of the general formula (XII)

$$X^1-R^1 \qquad (XII)$$

in which $R^1$ represents respectively optionally substituted alkyl, alkenyl, alkinyl or cycloalkyl and $X^1$ represents halogen, preferably chlorine, bromine or iodine at temperatures between 0° C. and 100° C., and the thus-obtained t-butylaminosulfonyl compounds of the general formula (XIII)

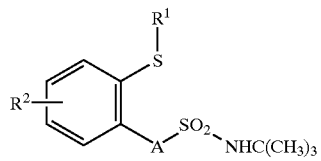

in which

A, $R^1$ and $R^2$ are each as defined above are then—preferably after intermediate isolation—reacted with a strong acid, such as for example trifluoroacetic acid, if appropriate in the presence of a diluent, such as for example methylene chloride, at temperatures between 0° C. and 50° C. (cf. the preparation examples).

The novel compounds of the formula (II) in which n represents zero, A represents a single bond and $R^1$ represents H are obtained when the t-butylaminosulfonyl compounds of the general formula (XI) are, as described above, reacted with sulfur after metallation, and the product formed of the general formula (XIV)

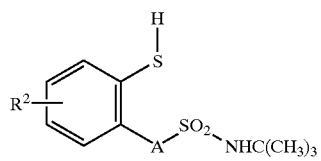

in which

A and $R^2$ are each as defined above is then—if appropriate after intermediate isolation—reacted with a strong acid, such as for example trifluoroacetic acid, if appropriate in the presence of a diluent, such as for example methylene chloride, at temperatures between 0° C. and 50° C., and the thus-obtained isomerization product of the general formula (XV)

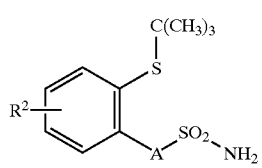

(XV)

in which

A and $R^2$ are each as defined above is—if appropriate after intermediate isolation—reacted with a Lewis acid, such as for example boron(III) bromide, in the presence of a diluent, such as for example methylene chloride, at temperatures between 0° C. and 50° C. (cf. the preparation examples).

The novel compounds of the formula (II) in which n represents zero, A represents a single bond and $R^1$ represents hydrogen or respectively optionally substituted alkyl, alkenyl, alkinyl or cycloalkyl are obtained when the t-butylaminosulfonyl compounds of the general formula (XI) are, as described above, reacted with sulfur after metallation, and the products formed of the general formula (IV)—above—are then—if appropriate after intermediate isolation—reacted with a suitable oxidizing agent, such as for example dimethyl sulfoxide, at temperatures between 20° C. and 120° C., and the disulfides formed of the general formula (XVI)

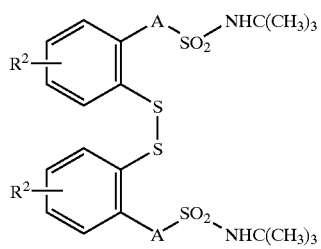

(XVI)

in which

A and $R^2$ are each as defined above are then—if appropriate after intermediate isolation—reacted with a strong acid, such as for example trifluoroacetic acid, if appropriate in the presence of a diluent, such as for example methylene chloride, at temperatures between 0° C. and 50° C., and the disulfides formed of the general formula (XVII)

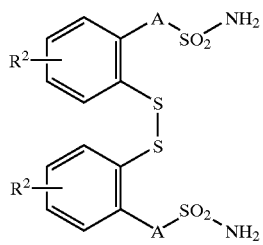

(XVII)

in which

A and $R^2$ are each as defined above are then—if appropriate after intermediate isolation—reacted with a reducing agent, such as for example sodium tetrahydridoborate (sodium borohydride), if appropriate in the presence of a diluent, such as for example methanol, at temperatures between 0° C. and 50° C., and the thus-obtained compounds of the formula (II) in which $R^1$ represents hydrogen are then, if appropriate, reacted with an alkylating agent of the general formula (XII)

$$X^1-R^1 \quad (XII)$$

in which $R^1$ represents respectively optionally substituted alkyl, alkenyl, alkinyl or cycloalkyl and $X^1$ represents halogen, preferably chlorine, bromine or iodine at temperatures between 0° C. and 100° C. (cf. the preparation examples).

The novel aminosulfonyl compounds of the formula (II) in which A represents a single bond, $R^1$ represents respectively optionally substituted alkyl, alkenyl, alkinyl or cycloalkyl and $R^2$ represents respectively optionally substituted alkyl, alkenyl or alkinyl—in position 6—are obtained when t-butylaminosulfonyl compounds of the general formula (XVIII)

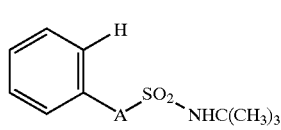

(XVIII)

in which

A is as defined above are metallated—i.e. the hydrogen atom shown in the formula (XVIII) is replaced by a metal atom—with a metalloorganic compound, such as for example butyl-lithium in hexane, if appropriate in the presence of a (further) inert diluent, such as for example tetrahydrofuran, and under an inert gas atmosphere, such as for example argon, at temperatures between −50° C. and +20° C., and then, in the same reaction medium, reacted with sulfur—i.e. the metal atom is replaced by sulfur—at temperatures between −30° C. and +30° C., and then, in the same reaction medium, reacted with an alkylating agent of the general formula (XII)

$$X^1-R^1 \quad (XII)$$

in which $R^1$ represents respectively optionally substituted alkyl, alkenyl, alkinyl or cycloalkyl and $X^1$ represents halogen, preferably chlorine, bromine or iodine at temperatures between 0° C. and 100° C. and the thus-obtained t-butylaminosulfonyl compounds of the general formula (XIX)

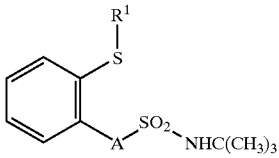

(XIX)

in which
A and $R^1$ are each as defined above, are then—preferably after intermediate isolation—metallated with an organometallic compound, such as for example butyllithium in hexane, if appropriate in the presence of a (further) inert diluent, such as for example tetrahydrofuran, and under an inert gas atmosphere, such as for example under argon, at temperatures between −50° C. and +20° C. and then, in the same reaction medium, reacted with an alkylating agent of the general formula (XX)

$$X^2—R^2 \qquad (XX)$$

in which
$R^2$ represents respectively optionally substituted alkyl, alkenyl or alkinyl and
$X^2$ represents halogen, preferably chloro, bromo or iodo at temperatures between 0° C. and 100° C. (cf. the preparation examples).

The compounds of the formula (II) in which n represents zero can be converted in a conventional manner into the corresponding compounds of the formula (II) in which n represents 1 or 2 by reaction with suitable oxidizing agents, such as for example 3-chloro-perbenzoic acid (cf. the preparation examples).

Some of the n-butylaminosulfonyl compounds of the formula (XIV)—above—required as precursors can also be obtained by reacting suitable disulfides of the formula (XVI)—above—with suitable alkylating agents of the formula (XII)—above—in the presence of sodium hydroxymethanesulfinate dihydrate and in the presence of disodium hydrogen phosphate and in the presence of a diluent, such as for example N,N-dimethyl-formamide (cf. the preparation examples).

A general definition of the (thio)carboxylic acid derivatives also to be used as starting materials in the process (a) according to the invention for the preparation of compounds of the formula (I) is given by the formula (III). In the formula (III), Q and $R^3$ preferably or in particular have that meaning which has already been indicated above, in connection with the description of the compounds of the formula (I) according to the invention, as being preferable or, respectively, particularly preferable for Q and $R^3$; Z preferably represents fluoro, chloro, bromo, $C_1$–$C_4$-alkoxy, phenoxy or benzyloxy, and in particular chloro, methoxy, ethoxy or phenoxy.

The starting materials of the formula (III) are known and/or can be prepared by methods known per se (cf. EP 459244, EP 341489, EP 422469, EP 425948, EP 431291, EP 507171, EP 534266).

A general definition of the sulfonyl iso(thio)cyanates to be used as starting materials in the process (b) according to the invention for the preparation of the compounds of the formula (I) is given by the formula (IV). In the formula (IV), n, A, Q, $R^1$ and $R^2$ preferably or in particular have that meaning which has already been indicated above, in connection with the description of the compounds of the formula (I) according to the invention, as being preferable or particularly preferable for n, A, Q, $R^1$ and $R^2$.

With the exception of the compound 2,6-bis-methylthiophenylsulfonyl isocyanate (cf. EP 135332), the starting materials of the formula (IV) have not to date been disclosed in the literature; with the exception of 2,6-bis-methylthiophenylsulfonyl isocyanate, they are novel substances and likewise form part of the subject matter of the present application.

The novel sulfonyl iso(thio)cyanates of the formula (IV) are obtained when aminosulfonyl compounds of the general formula (II)—above—are reacted with phosgene or thiophosgene, if appropriate in the presence of an alkyl isocyanate, such as for example butyl isocyanate, if appropriate in the presence of a reaction auxiliary, such as for example diazabicyclo[2.2.2]octane, and in the presence of a diluent, such as for example toluene, xylene or chlorobenzene, at temperatures between 80° C. and 150° C., and, after the reaction has ended, the volatile components are distilled off under reduced pressure.

A general definition of the heterocycles also to be used as starting materials in the processes (b), (c), (e) and (f) according to the invention for preparing the compounds of the formula (I) is given by the formula (V). In the formula (V), $R^3$ preferably or in particular has that meaning which has already been indicated above, in connection with the description of the compounds of the formula (I) according to the invention, as being preferable or particularly preferable for $R^3$.

The starting materials of the formula (V) are known and/or can be prepared by methods known per se (cf. EP 341489, EP 422469, EP 425948, EP 431291, EP 507171, EP 534266).

A general definition of the chlorosulfonyl compounds to be used as starting materials in the processes (c) and (d) according to the invention for preparing compounds of the formula (I) is given by the formula (VI). In the formula (VI), n, A, $R^1$ and $R^2$ preferably or in particular have that meaning which has already been indicated above, in connection with the description of the compounds of the formula (I) according to the invention, as being preferable or particularly preferable for n, A, $R^1$ and $R^2$.

The starting materials of the formula (VI) have not to date been disclosed in the literature; as novel substances they are likewise part of the subject matter of the present application.

The novel chlorosulfonyl compounds of the formula (VI) are obtained when the corresponding amino compounds of the general formula (XXI)

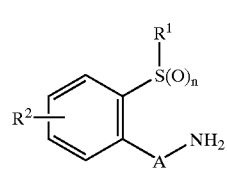

(XXI)

in which
A, $R^1$ and $R^2$ are as defined above are reacted with an alkali metal nitrite, such as for example sodium nitrite, in the presence of hydrochloric acid at temperatures between −10° C. and +10° C. and the diazonium salt solution thus obtained is reacted with sulfur dioxide in the presence of diluent, such as for example dichloromethane, 1,2-dichloro-ethane or acetic acid, and in the presence of a catalyst, such as for example copper(I)chloride and/or copper(II)chloride, at temperatures between −10° C. and +50° C.

A general definition of the (thio)carboxamides to be used as starting materials in the process (d) according to the invention for the preparation of the compounds of the formula (I) is given by the formula (VIII). In the formula (VIII), Q and $R^3$ preferably or in particular have that meaning which has already been indicated above, in connection with the description of the compounds of the formula (I) according to the invention, as being preferable or particularly preferable for Q and $R^3$.

The starting materials of the formula (VIII) are known and/or can be prepared by methods known per se (cf. EP 459244).

A general definition of the sulfonylamino(thio)carbonyl compounds to be used as starting materials in the process (e) according to the invention for the preparation of the compounds of the formula (I) is given by the formula (IX). In the formula (IX), n, A, Q, $R^1$ and $R^2$ preferably or in particular have that meaning which has already been indicated above, in connection with the description of the compounds of the formula (I) according to the invention, as being preferable or particularly preferable for n, A, Q, $R^1$ and $R^2$; Z preferably represents fluoro, chloro, bromo, $C_1$–$C_4$-alkoxy, phenoxy or benzyloxy, and in particular represents chloro, methoxy, ethoxy or phenoxy.

The starting materials of the formula (IX) are known and/or can be prepared by methods known per se.

A general definition of the benzene derivatives to be used as starting materials in the process (f) according to the invention for the preparation of the compounds of the formula (I) is given by the formula (X). In the formula (X), n, A, $R^1$ and $R^2$ preferably or in particular have that meaning which has already been indicated above, in connection with the description of the compounds of the formula (I) according to the invention, as being preferable or particularly preferable for n, A, $R^1$ and $R^2$.

The starting materials of the formula (X) are known and/or can be prepared by methods known per se.

The processes (a), (b), (c), (d), (e) and (f) according to the invention for the preparation of the novel compounds of the formula (I) are preferably carried out using diluents. Suitable diluents in this context are virtually all inert organic solvents. These include, preferably, aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, tetrachloromethane, chlorobenzene and o-dichlorobenzene; ethers such as diethyl ether and dibutyl ether, glycol dimethyl ether and diglycol dimethyl ether, tetrahydrofuran and dioxane; ketones such as acetone, methyl ethyl ketone, methyl isopropyl ketone and methyl isobutyl ketone; esters such as methyl acetate and ethyl acetate; nitriles, for example acetonitrile and propionitrile; amides, for example dimethylformamide, dimethylacetamide and N-methylpyrrolidone, and also dimethyl sulfoxide, tetramethylene sulfone and hexamethylphosphoric triamide.

Suitable reaction auxiliaries and/or acid acceptors for the processes (a), (b), (c), (d), (e) and (f) according to the invention are all acid-binding agents which are conventionally used for such reactions. Preference is given to alkali metal hydroxides, such as for example sodium hydroxide and potassium hydroxide, alkaline earth metal hydroxides, such as for example calcium hydroxide, alkali metal carbonates and alkoxides, such as sodium carbonate and potassium carbonate, sodium tert-butoxide and potassium tert-butoxide, and also basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo[4.3.0]-non-5-ene (DBN), 1,8-diazabicyclo[5.4.0]-undec-7-ene (DBU) and 1,4-diazabicyclo-[2.2.2]-octane (DABCO).

The reaction temperatures in the processes (a), (b), (c), (d), (e) and (f) according to the invention can be varied within a relatively wide range. The processes are in general carried out at temperatures of between −20° C. and +150° C., preferably at temperatures between 0° C. and +100° C.

The processes (a), (b), (c), (d), (e) and (f) according to the invention are generally carried out under atmospheric pressure. However, it is also possible to operate under elevated or reduced pressure.

For carrying out processes (a), (b), (c), (d), (e) and (f) according to the invention, the starting materials required in each case are in general employed in approximately equimolar quantities. However, it is also possible to use one of the components employed in each case in a relatively large excess. The reactions are in general carried out in a suitable diluent in the presence of an acid acceptor, and the reaction mixture is stirred for a number of hours at the particular temperature required. Work-up in the case of the processes (a), (b), (c), (d), (e) and (f) according to the invention is in each case carried out by customary methods (cf. the Preparation Examples).

Salts of the compounds of the general formula (I) according to the invention can be prepared if desired. Such salts are obtained in a simple manner by customary methods of forming salts, for example by dissolving or dispersing a compound of the formula (I) in an appropriate solvent, for example methylene chloride, acetone, tert-butyl methyl ether or toluene, and adding an appropriate base. The salts can then—if desired after prolonged stirring—be isolated by concentration or filtration with suction.

The active compounds according to the invention can be used as defoliants, desiccants, haulm killers and, especially, as weed-killers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledonous Weeds of the Genera

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous Cultures of the Genera

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous Weeds of the Genera

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous Cultures of the Genera

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective control of weeds in annual cultures.

The compounds of the formula (I) according to the invention are suitable for controlling monocotyledonous and dicotyledonous weeds, both pre-emergence and post-emergence. They exhibit strong herbicidal action and a broad spectrum of activity when used on the soil and on aerial parts of the plants.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-formning agents.

In the case of the use of water as an extender, organic solvents can, for example, also be used as auxiliary solvents. As liquid solvents, there are suitable in the main: aromatics, such as xylene, toluene or alkylnaplthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water.

Suitable solid carriers are:

for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as protein hydrolyzates; suitable dispersing agents are: for example lignin-sulfite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations in general contain between 0.1 and 95 percent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example anilides, such as diflufenican and propanil; arylcarboxylic acids, such as dichloropicolinic acid, dicamba and picloram; aryloxyalkanoic acids, such as 2,4-D, 2,4-DB, 2,4-DP, fluroxypyr, MCPA, MCPP and triclopyr; aryloxy-phenoxy-alkanoic esters, such as diclofop-methyl, fenoxaprop-ethyl, fluazifop-butyl, haloxyfop-methyl and quizalofop-ethyl; azinones, such as chloridazon and norflurazon; carbamates, such as chlorpropham, desmedipham, phenmedipham and propham; chloroacetanilides, such as alachlor, acetochlor, butachlor, metazachlor, metolachlor, pretilachlor and propachlor; dinitroanilines, such as oryzalin, pendimethalin and trifluralin; diphenyl ethers, such as acifluorfen, bifenox, fluoroglycofen, fomesafen, halosafen, lactofen and oxyfluorfen; ureas, such as chlorotoluron, diuron, fluometuron, isoproturon, linuron and methabenzthiazuron; hydroxylamines, such as alloxydim, clethodim, cycloxydim, sethoxydim and tralkoxydim; imidazolinones, such as imazethapyr, imazarnethabenz, imazapyr and imazaquin; nitriles, such as bromoxynil, dichlobenil and ioxynil; oxyacetamides, such as mefenacet; sulfonylureas, such as amidosulfuron, bensulfuron-methyl, chlorimuron-ethyl, chlorsulfuron, cinosulfuiron, metsulfuron-methyl, nicosulfuron, primisulfuron, pyrazosulfiron-ethyl, thifensulfuron-methyl, triasulfuron and tribenuron-methyl; thiocarbamates, such as butylate, cycloate, diallate, EPTC, esprocarb, molinate, prosulfocarb, thiobencarb and triallate; triazines, such as atrazine, cyanazine, simazine, simetryne, terbutryne and terbutylazine; triazinones, such as hexazinone, metamitron and metribuzin; and others, such as aminotriazole, benfuresate, bentazone, cinimethylin, clomazone, clopyralid, difenzoquat, dithiopyr, ethoflimesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by fisher dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and use of the active compounds according to the invention can be seen from the following examples.

PREPARATION EXAMPLES

Example 1

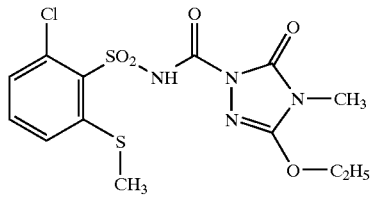

A solution of 3.3 g (14 mmol) of 2-chloro-6-methylthio-benzenesulfonamide, 3.7 g (14 mmol) of 5-ethoxy-4-methyl-2-phenoxycarbonyl-2,4-dihydro-3H-1,2,4-triazol-3-one and 2.3 g (15.4 mmol) of diazabicyclo[5.4.0]undecene (DBU) in 30 ml of acetonitrile is stirred at room temperature (about 20° C.) for six hours. The solvent is then removed using water pump vacuum and the oily residue is taken up in 100 ml of methylene chloride. The solution is washed successively with 1N hydrochloric acid and saturated brine, dried over sodium sulfate and freed from the solvent using water pump vacuum. 6.6 g of an oily residue are obtained, which crystallizes when stirred with 30 ml of ethanol. After filtration and drying under reduced pressure at 25° C., 3.15 g (55.4% of theory) of 5-ethoxy-4-methyl-2-(2-chloro-6-methylthio-phenylsulfonyl-aminocarbonyl)-2,4-dihydro-3H-1,2,4-triazol-3-one of melting point 144° C. are obtained.

Similar to Preparation Example 1 and in accordance with the general description of the preparation processes according to the invention, it is also possible to prepare for example the compounds of the formula (I) listed in Table 1 below.

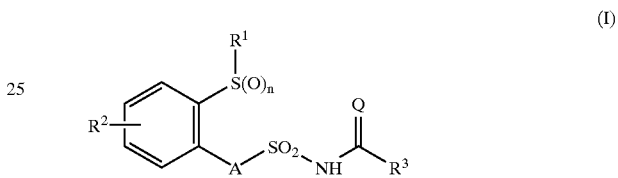

(I)

TABLE 1

Examples of the compounds of the formula (I)

| Ex. No. | n | A | Q | R¹ | (Position-) R² | R³ | Melting point (° C.) |
|---|---|---|---|---|---|---|---|
| 2 | 0 | — | O | C₂H₅ | (6-)OCH₃ | ![](N-O ring with CH₃) | 89 |
| 3 | 0 | — | O | C₂H₅ | (6-)OCF₃ | ![](N-O ring with CH₃) | 111 (pyridine salt) |
| 4 | 0 | — | O | C₂H₅ | (6-)OCF₃ | ![](N-O ring with CH₃) | 112 |
| 5 | 2 | — | O | N(CH₃)₂ | (4-)SO₂N(CH₃)₂ | ![](triazolone with OC₂H₅) | 189 |

TABLE 1-continued

Examples of the compounds of the formula (I)

| Ex. No. | n | A | Q | R¹ | (Position-) R² | R³ | Melting point (° C.) |
|---|---|---|---|---|---|---|---|
| 6 | 0 | — | O | $C_2H_5$ | (6-)$OCF_3$ | 1,4-dimethyl-5-ethoxy-1,2,4-triazol-3(2H)-one | 127 |
| 7 | 0 | — | O | $C_2H_5$ | (6-)$OCH_3$ | 1,4-dimethyl-5-ethoxy-1,2,4-triazol-3(2H)-one | 149 |
| 8 | 0 | — | O | $C_2H_5$ | (6-)$OCH_3$ | 1,4-dimethyl-5-ethyl-1,2,4-triazol-3(2H)-one | 140 |
| 9 | 0 | — | O | $C_2H_5$ | (6-)F | 1,4-dimethyl-5-ethoxy-1,2,4-triazol-3(2H)-one | 139 |
| 10 | 0 | — | O | $C_2H_5$ | (6-)Cl | 1,4-dimethyl-5-ethoxy-1,2,4-triazol-3(2H)-one | 114 |
| 11 | 0 | — | O | $C_2H_5$ | (6-)$CF_3$ | 1,4-dimethyl-5-ethoxy-1,2,4-triazol-3(2H)-one | 119 |
| 12 | 2 | — | O | $C_2H_5$ | (6-)$CF_3$ | 1,4-dimethyl-5-ethoxy-1,2,4-triazol-3(2H)-one | 142 |
| 13 | 0 | — | O | $C_2H_5$ | (6-)$CF_3$ | 1,4-dimethyl-5-methoxy-1,2,4-triazol-3(2H)-one | 146 |

TABLE 1-continued

Examples of the compounds of the formula (I)

| Ex. No. | n | A | Q | R¹ | (Position-) R² | R³ | Melting point (° C.) |
|---|---|---|---|---|---|---|---|
| 14 | 0 | — | O | $C_2H_5$ | (6-)$CF_3$ | 1,4-dimethyl-5-(methylthio)-1,2,4-triazol-3(4H)-one | 169 |
| 15 | 0 | — | O | $C_2H_5$ | (6-)$CF_3$ | 5-ethyl-1,4-dimethyl-1,2,4-triazol-3(4H)-one | 135 |
| 16 | 0 | — | O | $C_2H_5$ | (6-)F | 5-methoxy-1,4-dimethyl-1,2,4-triazol-3(4H)-one | 130 |
| 17 | 0 | — | O | $C_2H_5$ | (6-)F | 1,4-dimethyl-5-(methylthio)-1,2,4-triazol-3(4H)-one | 120 |
| 18 | 0 | — | O | $i\text{-}C_3H_7$ | (6-)$OCH_3$ | 5-ethoxy-1,4-dimethyl-1,2,4-triazol-3(4H)-one | 145 |
| 19 | 0 | — | O | $C_2H_5$ | (6-)Cl | 5-methoxy-1,4-dimethyl-1,2,4-triazol-3(4H)-one | 133 |
| 20 | 0 | — | O | $CH_3$ | (6-)$OCH_3$ | 5-ethoxy-1,4-dimethyl-1,2,4-triazol-3(4H)-one | 113 |
| 21 | 0 | — | O | $CH_3$ | (6-)$OCH_3$ | 5-methoxy-1,4-dimethyl-1,2,4-triazol-3(4H)-one | 168 |

TABLE 1-continued

Examples of the compounds of the formula (I)

| Ex. No. | n | A | Q | R¹ | (Position-) R² | R³ | Melting point (° C.) |
|---|---|---|---|---|---|---|---|
| 22 | 0 | — | O | CH₃ | (6-)OCH₃ | 1,4-dimethyl-5-ethyl-1,2,4-triazol-3(4H)-one | 122 |
| 23 | 0 | — | O | i-C₃H₇ | (6-)OCH₃ | 1,4-dimethyl-5-ethyl-1,2,4-triazol-3(4H)-one | 146 |
| 24 | 0 | — | O | i-C₃H₇ | (6-)OCH₃ | 1,4-dimethyl-5-methoxy-1,2,4-triazol-3(4H)-one | 175 |
| 25 | 0 | — | O | i-C₃H₇ | (6-)OCF₃ | 1,4-dimethyl-5-ethoxy-1,2,4-triazol-3(4H)-one | 125 |
| 26 | 0 | — | O | i-C₃H₇ | (6-)CH₃ | 1,4-dimethyl-5-ethyl-1,2,4-triazol-3(4H)-one | 133 |
| 27 | 0 | — | O | i-C₃H₇ | (6-)CH₃ | 1,4-dimethyl-5-methoxy-1,2,4-triazol-3(4H)-one | 144 |
| 28 | 0 | — | O | i-C₃H₇ | (6-)CH₃ | 1,4-dimethyl-5-ethoxy-1,2,4-triazol-3(4H)-one | 131 |
| 29 | 0 | — | O | i-C₃H₇ | (6-)CH₃ | 1,4-dimethyl-5-methylthio-1,2,4-triazol-3(4H)-one | 121 |

TABLE 1-continued

Examples of the compounds of the formula (I)

| Ex. No. | n | A | Q | R¹ | (Position-)R² | R³ | Melting point (° C.) |
|---|---|---|---|---|---|---|---|
| 30 | 0 | — | O | C₂H₅ | (6-)OCH₃ | 1,4-dimethyl-5-methoxy-1,2,4-triazol-3(2H)-one | 173 |
| 31 | 0 | — | O | C₂H₅ | (6-)OCH₃ | 1,4-dimethyl-5-methylthio-1,2,4-triazol-3(2H)-one | 113 |
| 32 | 0 | — | O | CH₃ | (6-)OCF₃ | 1,4-dimethyl-5-methoxy-1,2,4-triazol-3(2H)-one | 148 |
| 33 | 0 | — | O | CH₃ | (6-)OCF₃ | 1,4-dimethyl-5-methylthio-1,2,4-triazol-3(2H)-one | 147 |
| 34 | 0 | — | O | CH₃ | (6-)OCF₃ | 1,4-dimethyl-5-ethyl-1,2,4-triazol-3(2H)-one | 127 |
| 35 | 0 | — | O | CH₃ | (6-)OCF₃ | 1,4-dimethyl-5-ethoxy-1,2,4-triazol-3(2H)-one | 138 |
| 36 | 0 | — | O | i-C₃H₇ | (6-)C₂H₅ | 1,4-dimethyl-5-ethoxy-1,2,4-triazol-3(2H)-one | 141 |
| 37 | 0 | — | O | i-C₃H₇ | (6-)SCH₃ | 1,4-dimethyl-5-ethyl-1,2,4-triazol-3(2H)-one | 163 |

TABLE 1-continued

Examples of the compounds of the formula (I)

| Ex. No. | n | A | Q | R¹ | (Position-) R² | R³ | Melting point (° C.) |
|---|---|---|---|---|---|---|---|
| 38 | 0 | — | O | i-C₃H₇ | (6-)SCH₃ | 1,4-dimethyl-5-ethoxy-1,2,4-triazol-3(2H)-one | 143 |
| 39 | 0 | — | O | C₂H₅ | (6-)OCF₃ | 1,4-dimethyl-5-ethyl-1,2,4-triazol-3(2H)-one | 101 |
| 40 | 0 | — | O | C₂H₅ | (6-)OCF₃ | 1,4-dimethyl-5-methoxy-1,2,4-triazol-3(2H)-one | 116 |
| 41 | 0 | — | O | C₂H₅ | (6-)OCF₃ | 1,4-dimethyl-5-methylthio-1,2,4-triazol-3(2H)-one | 115 |
| 42 | 0 | — | O | i-C₃H₇ | (6-)OCH₃ | 1,4-dimethyl-5-methylthio-1,2,4-triazol-3(2H)-one | >230 (d.) |
| 43 | 0 | — | O | C₂H₅ | (6-)SC₂H₅ | 1,4-dimethyl-5-ethoxy-1,2,4-triazol-3(2H)-one | 134 |
| 44 | 0 | — | O | C₂H₅ | (6-)SC₂H₅ | 1,4-dimethyl-5-ethyl-1,2,4-triazol-3(2H)-one | 153 |
| 45 | 0 | — | O | C₂H₅ | (6-)SC₂H₅ | 1,4-dimethyl-5-methylthio-1,2,4-triazol-3(2H)-one | 150 |

TABLE 1-continued

Examples of the compounds of the formula (I)

| Ex. No. | n | A | Q | R¹ | (Position-) R² | R³ | Melting point (° C.) |
|---|---|---|---|---|---|---|---|
| 46 | 0 | — | O | $C_2H_5$ | (6-)$SC_2H_5$ | 1,4-dimethyl-5-methoxy-1,2,4-triazol-3(4H)-one | 168 |
| 47 | 0 | — | O | $-C_2H_4O-COCF_3$ | (6-)$SC_2H_5$ | 1,4-dimethyl-5-ethoxy-1,2,4-triazol-3(4H)-one | 162 |
| 48 | 0 | — | O | $CH_3$ | (6-)$CH_3$ | 1,4-dimethyl-5-ethoxy-1,2,4-triazol-3(4H)-one | 165 |
| 49 | 0 | — | O | $CH_3$ | (6-)$CH_3$ | 1,4-dimethyl-5-ethyl-1,2,4-triazol-3(4H)-one | 141 |
| 50 | 0 | — | O | $CH_3$ | (6-)$SCH_3$ | 1,4-dimethyl-5-methoxy-1,2,4-triazol-3(4H)-one | 188 |
| 51 | 0 | — | O | $CH_3$ | (6-)$SCH_3$ | 1,4-dimethyl-5-methylthio-1,2,4-triazol-3(4H)-one | 162 |
| 52 | 0 | — | O | $CH_3$ | (6-)$SCH_3$ | 1,4-dimethyl-5-ethoxy-1,2,4-triazol-3(4H)-one | 183 |
| 53 | 0 | — | O | $C_2H_5$ | (6-)$CH_3$ | 1,4-dimethyl-5-methoxy-1,2,4-triazol-3(4H)-one | 157 |

TABLE 1-continued

Examples of the compounds of the formula (I)

| Ex. No. | n | A | Q | R¹ | (Position-) R² | R³ | Melting point (°C.) |
|---|---|---|---|---|---|---|---|
| 54 | 0 | — | O | $C_2H_5$ | (6-)$CH_3$ | 1,4-dimethyl-5-(methylthio)-1,2,4-triazol-3(4H)-one | 126 |
| 55 | 0 | — | O | $C_2H_5$ | (6-)$CH_3$ | 5-ethyl-1,4-dimethyl-1,2,4-triazol-3(4H)-one | 149 |
| 56 | 0 | — | O | $C_2H_5$ | (6-)$CH_3$ | 5-ethoxy-1,4-dimethyl-1,2,4-triazol-3(4H)-one | 154 |
| 57 | 0 | — | O | $CH_2CH_2F$ | (6-)$OCH_3$ | 5-methoxy-1,4-dimethyl-1,2,4-triazol-3(4H)-one | 192 |
| 58 | 0 | — | O | $CH_2CH_2F$ | (6-)$OCH_3$ | 5-ethyl-1,4-dimethyl-1,2,4-triazol-3(4H)-one | 147 |
| 59 | 0 | — | O | $CH_2CH_2F$ | (6-)$OCH_3$ | 5-ethoxy-1,4-dimethyl-1,2,4-triazol-3(4H)-one | 171 |
| 60 | 0 | — | O | $t\text{-}C_4H_9$ | (6-)$CF_3$ | 5-ethoxy-1,4-dimethyl-1,2,4-triazol-3(4H)-one | 141 |
| 61 | 0 | — | O | $CH_3$ | (6-)$CF_3$ | 5-methoxy-1,4-dimethyl-1,2,4-triazol-3(4H)-one | 157 |

TABLE 1-continued

Examples of the compounds of the formula (I)

| Ex. No. | n | A | Q | $R^1$ | (Position-) $R^2$ | $R^3$ | Melting point (° C.) |
|---|---|---|---|---|---|---|---|
| 62 | 0 | — | O | $CH_3$ | (6-)$CF_3$ | 1,4-dimethyl-5-(methylthio)-1,2,4-triazol-3(4H)-one-yl | 173 |
| 63 | 0 | — | O | $CH_3$ | (6-)$CF_3$ | 1,4-dimethyl-5-ethyl-1,2,4-triazol-3(4H)-one-yl | 165 |
| 64 | 0 | — | O | $CH_3$ | (6-)$CF_3$ | 1,4-dimethyl-5-ethoxy-1,2,4-triazol-3(4H)-one-yl | 165 |
| 65 | 0 | — | O | $CH_2CH_2F$ | (6-)$OCF_3$ | 1,4-dimethyl-5-methoxy-1,2,4-triazol-3(4H)-one-yl | 112 |
| 66 | 0 | — | O | $CH_2CH_2F$ | (6-)$OCF_3$ | 1,4-dimethyl-5-(methylthio)-1,2,4-triazol-3(4H)-one-yl | 125 |
| 67 | 0 | — | O | $CH_2CH_2F$ | (6-)$OCF_3$ | 1,4-dimethyl-5-ethyl-1,2,4-triazol-3(4H)-one-yl | 95 |
| 68 | 0 | — | O | $CH_2CH_2F$ | (6-)$OCF_3$ | 1,4-dimethyl-5-ethoxy-1,2,4-triazol-3(4H)-one-yl | 137 |
| 69 | 0 | — | O | $CH_2CH_2F$ | (6-)$CF_3$ | 1,4-dimethyl-5-methoxy-1,2,4-triazol-3(4H)-one-yl | 151 |

TABLE 1-continued
Examples of the compounds of the formula (I)
| Ex. No. | n | A | Q | R¹ | (Position-) R² | R³ | Melting point (° C.) |
|---|---|---|---|---|---|---|---|
| 70 | 0 | — | O | CH$_2$CH$_2$F | (6-)CF$_3$ | 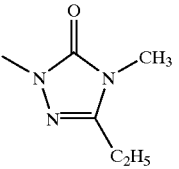 | 139 |
| 71 | 0 | — | O | CH$_2$CH$_2$F | (6-)CF$_3$ | 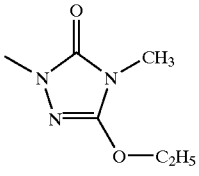 | 158 |
| 72 | 0 | — | O | i-C$_3$H$_7$ | (6-)CF$_3$ | 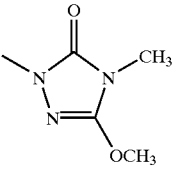 | 150 |
| 73 | 0 | — | O | i-C$_3$H$_7$ | (6-)CF$_3$ | 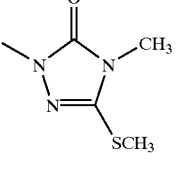 | 149 |
| 74 | 0 | — | O | i-C$_3$H$_7$ | (6-)CF$_3$ | 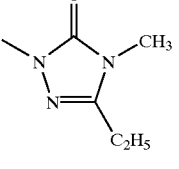 | 166 |
| 75 | 0 | — | O | i-C$_3$H$_7$ | (6-)CF$_3$ | 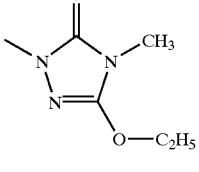 | 152 |
| 76 | 0 | — | O |  | (6-)OCF$_3$ | 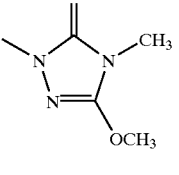 | 149 |
| 77 | 0 | — | O |  | (6-)OCF$_3$ | 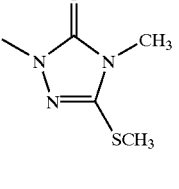 | 152 |

TABLE 1-continued
Examples of the compounds of the formula (I)
| Ex. No. | n | A | Q | R¹ | (Position-) R² | R³ | Melting point (° C.) |
|---|---|---|---|---|---|---|---|
| 78 | 0 | — | O |  | (6-)OCF₃ | 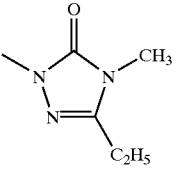 | 145 |
| 79 | 0 | — | O |  | (6-)OCF₃ | 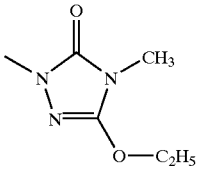 | 138 |
| 80 | 0 | — | O |  | (6-)OCF₃ | 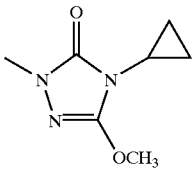 | 117 |
| 81 | 0 | — | O | C₂H₅ | (6-)OCF₃ | 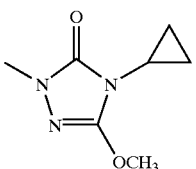 | 124 |
| 82 | 0 | — | O | C₂H₅ | (6-)OCH₃ | 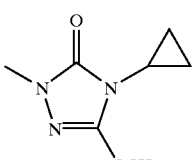 | 183 |
| 83 | 0 | — | O | CH₃ | (6-)Cl | 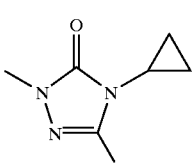 | 147 |
| 84 | 0 | — | O | CH₃ | (6-)OCF₃ | 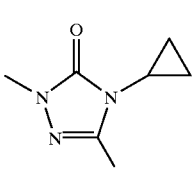 | 186 |
| 85 | 0 | — | O | CH₃ | (6-)OCH₃ | 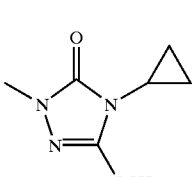 | 166 |

TABLE 1-continued
Examples of the compounds of the formula (I)
| Ex. No. | n | A | Q | R¹ | (Position-) R² | R³ | Melting point (° C.) |
|---|---|---|---|---|---|---|---|
| 86 | 0 | — | O | CH₂CH₂F | (6-)OCH₃ | 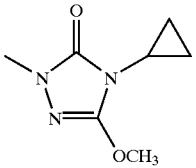 | 196 |
| 87 | 0 | — | O | CH₃ | (6-)CF₃ | 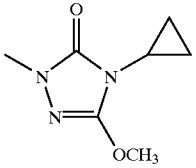 | 140 |
| 88 | 0 | — | O | CH₃ | (6-)SCH₃ | 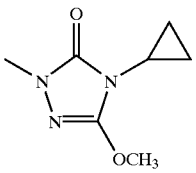 | 165 |
| 89 | 0 | — | O | CH₂CH₂F | (6-)OCF₃ | 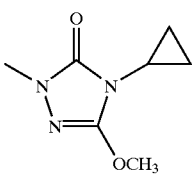 | 126 |
| 90 | 1 | — | O | C₂H₅ | (6-)CF₃ | 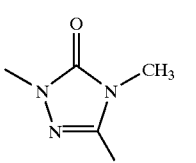 | 132 |
| 91 | 0 | — | O | CF₃ | (6-)OCF₃ | 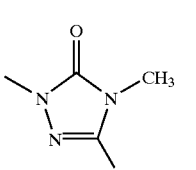 | 167 |
| 92 | 0 | — | O | (CH₂)₃F | (6-)CF₃ | 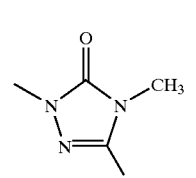 | 141 |
| 93 | 0 | — | O | (CH₂)₃F | (6-)CF₃ | 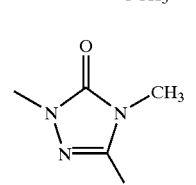 | 134 |

TABLE 1-continued

Examples of the compounds of the formula (I)

| Ex. No. | n | A | Q | R¹ | (Position-) R² | R³ | Melting point (° C.) |
|---|---|---|---|---|---|---|---|
| 94 | 0 | — | O | (CH$_2$)$_3$F | (6-)CF$_3$ | 1,4-dimethyl-5-ethoxy-1,2,4-triazol-3(2H)-one | 119 |
| 95 | 0 | — | O | CH$_2$F | (6-)OCF$_3$ | 1,4-dimethyl-5-ethoxy-1,2,4-triazol-3(2H)-one | 119 |
| 96 | 0 | — | O | CH$_2$F | (6-)OCF$_3$ | 1,4-dimethyl-5-methoxy-1,2,4-triazol-3(2H)-one | 133 |
| 97 | 0 | — | O | CH$_2$F | (6-)OCF$_3$ | 1-methyl-4-cyclopropyl-5-methoxy-1,2,4-triazol-3(2H)-one | 147 |
| 98 | 0 | — | O | CH$_2$CHF$_2$ | (6-)CF$_3$ | 1,4-dimethyl-5-ethoxy-1,2,4-triazol-3(2H)-one | 116 |
| 99 | 0 | — | O | CH$_2$CHF$_2$ | (6-)CF$_3$ | 1,4-dimethyl-5-methoxy-1,2,4-triazol-3(2H)-one | (log P = 2.59) |
| 100 | 0 | — | O | CH$_2$CHF$_2$ | (6-)CF$_3$ | 1-methyl-4-cyclopropyl-5-methoxy-1,2,4-triazol-3(2H)-one | (log P = 2.96) |
| 101 | 0 | — | O | CH$_2$CHF$_2$ | (6-)CH$_3$ | 1,4-dimethyl-5-methylthio-1,2,4-triazol-3(2H)-one | (log P = 2.73) |

TABLE 1-continued

Examples of the compounds of the formula (I)

| Ex. No. | n | A | Q | R¹ | (Position-) R² | R³ | Melting point (° C.) |
|---|---|---|---|---|---|---|---|
| 102 | 2 | — | O | N(CH$_3$)$_2$ | (6-)CH$_3$ | 1,2,4-triazol-3(2H)-one, 2,4-dimethyl-5-ethyl | 203 (d.) |
| 103 | 2 | — | O | N(CH$_3$)$_2$ | (6-)CH$_3$ | 1,2,4-triazol-3(2H)-one, 2,4-dimethyl-5-ethoxy | 146 |
| 104 | 2 | — | O | N(CH$_3$)$_2$ | (6-)CH$_3$ | 1,2,4-triazol-3(2H)-one, 2,4-dimethyl-5-SCH$_3$ | 208 |
| 105 | 2 | — | O | N(CH$_3$)$_2$ | (6-)CH$_3$ | 1,2,4-triazol-3(2H)-one, 2-methyl-4-cyclopropyl-5-OC$_2$H$_5$ | 137 |
| 106 | 2 | — | O | N(CH$_3$)$_2$ | (6-)CH$_3$ | 1,2,4-triazol-3(2H)-one, 2-methyl-4-cyclopropyl-5-CH$_2$OCH$_3$ | 137 |
| 107 | 2 | — | O | N(CH$_3$)$_2$ | (6-)CH$_3$ | 1,2,4-triazol-3(2H)-one, 2,4-dimethyl-5-OCH$_3$ | 182 (d.) |
| 108 | 2 | — | O | N(CH$_3$)$_2$ | (6-)CH$_3$ | 1,2,4-triazol-3(2H)-one, 2,4-dimethyl-5-C$_3$H$_7$-n | 113 |
| 109 | 2 | — | O | N(CH$_3$)$_2$ | (6-)CH$_3$ | 1,2,4-triazol-3(2H)-one, 2,4-dimethyl-5-C$_3$H$_7$-i | 80 |

TABLE 1-continued

Examples of the compounds of the formula (I)

| Ex. No. | n | A | Q | R¹ | (Position-) R² | R³ | Melting point (° C.) |
|---|---|---|---|---|---|---|---|
| 110 | 2 | — | O | N(CH$_3$)$_2$ | (6-)CH$_3$ | 1-methyl-4-ethyl-5-ethoxy-1,2,4-triazol-3(4H)-one | 114 |
| 111 | 2 | — | O | N(CH$_3$)$_2$ | (6-)CH$_3$ | 1-methyl-4-methyl-5-(n-propoxy)-1,2,4-triazol-3(4H)-one | 138 |
| 112 | 2 | — | O | N(CH$_3$)$_2$ | (6-)CH$_3$ | 1-methyl-4-methyl-5-(i-propoxy)-1,2,4-triazol-3(4H)-one | 161 |
| 113 | 0 | — | O | CH$_3$ | (6-)CF$_3$ | 1-methyl-4-methyl-5-methylthio-1,2,4-triazol-3(4H)-one | >210 (d.) |
| 114 | 0 | — | O | CF$_3$ | (6-)CF$_3$ | 1-methyl-4-methyl-5-methoxy-1,2,4-triazol-3(4H)-one | 169 |
| 115 | 0 | — | O | CF$_3$ | (6-)CF$_3$ | 1-methyl-4-methyl-5-methylthio-1,2,4-triazol-3(4H)-one | 159 |
| 116 | 0 | — | O | CF$_3$ | (6-)CF$_3$ | 1-methyl-4-methyl-5-ethyl-1,2,4-triazol-3(4H)-one | 161 |
| 117 | 0 | — | O | CF$_3$ | (6-)CF$_3$ | 1-methyl-4-methyl-5-ethoxy-1,2,4-triazol-3(4H)-one | 175 |

TABLE 1-continued
Examples of the compounds of the formula (I)
| Ex. No. | n | A | Q | R¹ | (Position-) R² | R³ | Melting point (° C.) |
|---|---|---|---|---|---|---|---|
| 118 | 0 | — | O | CF₃ | (6-)CF₃ | 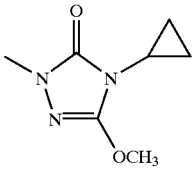 | 158 |
| 119 | 0 | — | O | CH₃ | (6-)C₂H₅ | 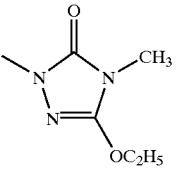 | 142 |
| 120 | 0 | — | O | CH₂CH₂F | (6-)OC₃H₇-n | 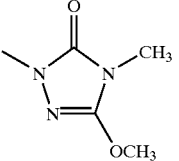 | 133 |
| 121 | 0 | — | 0 | CH₂CH₂F | (6-)OC₃H₇-n | 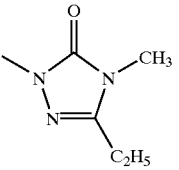 | 131 |
| 122 | 0 | — | O | CH₂CH₂F | (6-)OC₃H₇-n | 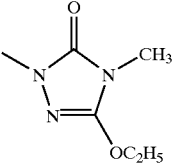 | 141 |
| 123 | 0 | — | O | CH₂CH₂F | (6-)OC₃H₇-n | 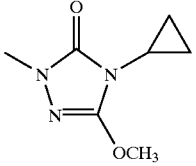 | 144 |
| 124 | 0 | — | O | CH₂CH₂F | (6-)OC₃H₇-i | 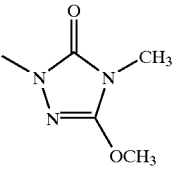 | 153 |
| 125 | 0 | — | O | CH₂CH₂F | (6-)OC₃H₇-i | 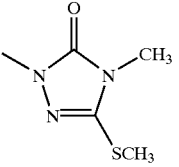 | 152 |

TABLE 1-continued

Examples of the compounds of the formula (I)

| Ex. No. | n | A | Q | R$^1$ | (Position-) R$^2$ | R$^3$ | Melting point (° C.) |
|---|---|---|---|---|---|---|---|
| 126 | 0 | — | O | CH$_2$CH$_2$F | (6-)OC$_3$H$_7$-i | [triazolinone with N-CH$_3$, N-CH$_3$, C$_2$H$_5$] | 157 |
| 127 | 0 | — | O | CH$_2$CH$_2$F | (6-)OC$_3$H$_7$-i | [triazolinone with N-CH$_3$, N-CH$_3$, OC$_2$H$_5$] | 178 |
| 128 | 0 | — | O | CH$_2$CH$_2$F | (6-)OC$_3$H$_7$-i | [triazolinone with N-CH$_3$, N-cyclopropyl, OCH$_3$] | 142 |
| 129 | 0 | — | O | CH$_2$CH$_2$F | (6-)OCH$_3$ | [triazolinone with N-CH$_3$, N-CH$_3$, SCH$_3$] | 140 |
| 130 | 0 | — | O | CH$_3$ | (6-)CF$_3$ | [triazolinone with N-CH$_3$, N-CH$_3$, OC$_2$H$_5$] | 216 |

Comments (for Table 1):
[1] The group denoting the radical R$^1$ in the Examples 76–80 represents —CH$_2$—C≡CH (propargyl).
[2] d. = decomposition.
[3] log P = logarithm to base ten of the partition coefficient (P) of the dissolved substance in the two-phase system n-octanol/water, determined by the HPLC method (at pH 2; eluent: acetonitrile containing 1% of H$_3$PO$_4$ [cf. for example Official Journal of the European Communities, No. L 383A, 35, pages 63 ff., dated 29.12.1992].

The compound listed as Example 3 in Table 1 can be prepared, for example, as follows:

2.1 g (0.014 mol) of the sodium salt of 5-methyl-1,2,4-oxadiazole-3-carboxylic acid are refluxed with 80 ml of thionyl chloride and 5 drops of dimethylformamide, for 3 hours. The excess thionyl chloride is then distilled off under reduced pressure and the residue is taken up in 50 ml of pyridine while cooling. 4.2 g (0.014 mol) of 2-ethylmercapto-6-trifluoromethoxy-benzenesulfonamide are then added, and the reaction mixture is stirred at room temperature for 15 hours. The pH is adjusted to 1 using hydrochloric acid, and the product is filtered off under suction and washed with 1N hydrochloric acid.

After drying, 5.6 g (81% of theory) of N-(2-ethylmercapto-6-trifluoromethoxy-phenylsulfonyl)-5-methyl-1,2,4-oxadiazole-3-carboxamide are obtained as the pyridinium salt of melting point 111° C.

The compound listed as Example 4 in Table 1 can be prepared, for example, as follows:

3 g of the pyridinium salt prepared by the method of Example 3 are stirred with 60 ml of 10% strength aqueous potassium hydrogen carbonate solution for 12 hours. The solid formed is filtered off under suction, stirred with 50 ml of 1N hydrochloric acid, filtered off under suction, washed with water and dried.

2.3 g (76% of theory) of N-2-ethylmercapto-6-trifluoromethoxy-phenylsulfonyl)-5-methyl-1,2,4-oxadiazole-3-carboxamide of melting point 112° C. are obtained.

Starting Materials of the Formula (II)

Example (II-1)

Step 1

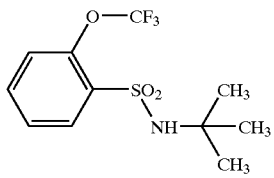

At 5° C., 38.9 g (0.384 mol) of triethylamine and 28.0 g (0.384 mol) of tert-butylamine are added dropwise in succession to a solution of 99.0 g (0.384 mol) of 2-trifluoromethoxy-benzenesulfonyl chloride in 400 ml of acetonitrile. The reaction mixture is stirred at room temperature (about 20° C.) for 16 hours and then concentrated using water pump vacuum. The oily residue is dissolved in dichloromethane and the solution is washed with 2N hydrochloric acid, dried over magnesium sulfate and filtered. Using water pump vacuum, the solvent is carefully distilled off from the filtrate.

107.6 g (95.3% of theory) of N-tert-butyl-2-trifluoromethoxy-benzenesulfonamide are obtained as a crystalline residue of melting point 137° C.

Step 2

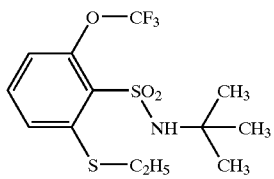

Under argon, 30.8 g (0.104 mol) of N-tert-butyl-2-trifluoromethoxy-benzenesulfonamide are dissolved in 280 ml of (anhydrous)tetrahydrofuran, cooled to −5° C. and treated with 156 ml (0.26 mol) of 15% strength n-butyllithium solution in hexane. After the solution has been stirred for 3 hours at from 0° C. to −5° C., 3.64 g (0.114 mol) of sulfur are added, and the solution is stirred for a further 3 hours at room temperature (about 20° C.). The reaction mixture is then treated with 18.0 g (0.115 mol) of iodoethane, stirred at room temperature for 16 hours and then treated with 560 ml of dichloromethane. The solution is washed with 2N hydrochloric acid, dried over magnesium sulfate and concentrated using water pump vacuum. The crude product obtained as a residue is stirred with petroleum ether, filtered off under suction and dried under reduced pressure.

31.4 g (84.6% of theory) of N-tert-butyl-2-ethylthio-6-trifluoromethoxy-benzenesulfonamide of melting point 77° C. are obtained.

Step 3

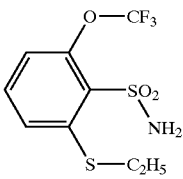

At room temperature (about 20° C.), 163 ml (2.13 mol) of trifluoroacetic acid are added dropwise to a solution of 30.4 g (0.085 mol) of N-tert-butyl-2-ethylthio-6-trifluoromethoxy-benzenesulfonamide in 160 ml of dichloromethane. The reaction mixture is stirred at room temperature for about 24 hours, diluted with 300 ml of dichloromethane, washed two times with 300 ml of water, dried over magnesium sulfate and concentrated using water pump vacuum. The crude product obtained as a residue is stirred with petroleum ether, filtered off under suction and dried under reduced pressure.

21.7 g (84.7% of theory) of 2-ethylthio-6-trifluoromethoxy-benzenesulfonamide of melting point 146° C. are obtained.

Example (II-2)

Step 1

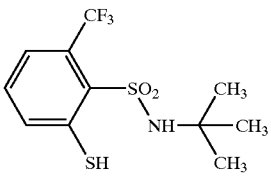

Under argon, 163.1 g (0.58 mol) of N-tert-butyl-2-trifluoromethyl-benzenesulfonamide are dissolved in 1 liter of (anhydrous)tetrahydrofuran, cooled to −10° C. and treated with 884 ml (1.45 mol) of 15% strength n-butyllithium solution in hexane. After the solution has been stirred for 3 hours at from 0° C. to −5° C., 30.7 g (0.96 mol) of sulfur are added, and the solution is stirred at room temperature (about 20° C.) for a further 20 hours. While cooling to about 20° C., the reaction mixture is then treated with 100 ml of 2N hydrochloric acid, 1 liter of water and 1 liter of dichloroinethane. The aqueous phase is adjusted to pH 1 using 2N hydrochloric acid, and the organic phase is separated off, washed with water, dried over magnesium sulfate and concentrated using water pump vacuum. The crude product obtained as a residue is stirred with petroleum ether, filtered off under suction and dried under reduced pressure.

160.4 g (84.6% of theory) of N-tert-butyl-2-mercapto-6-trifluoromethyl-benzenesulfonamide of melting point 139° C. are obtained.

Step 2

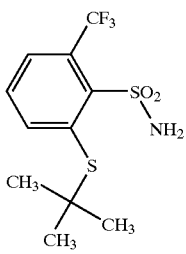

At room temperature (about 20° C.), 104 ml (1.36 mol) of trifluoroacetic acid are added dropwise to a solution of 17.0 g (0.054 mol) of N-tert-butyl-2-mercapto-6-17 trifluoromethyl-benzenesulfonamide in 100 ml of dichloromethane. The reaction mixture is stirred at room temperature for about 24 hours, diluted with 300 ml of dichloromethane, washed two times with 200 ml of water, dried over magnesium sulfate and concentrated using water pump vacuum. The crude product obtained as a residue is stirred with petroleum ether, filtered off under suction and dried under reduced pressure.

13.8 g (81.2% of theory) of 2-tert-butylthio-6-trifluoromethyl-benzenesulfonamide of melting point 91° C. are obtained.

Step 3

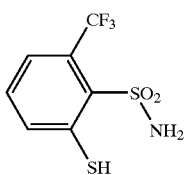

At room temperature (about 20° C.), 23.3 ml (0.023 mol) of a 1M boron tribromide solution in dichloromethane are added dropwise to a solution of 7.3 g (0.023 mol) of N-tert-butyl-2-tert-butylthio-6-trifluoromethyl-benzenesulfonamide in 80 ml of dichloromethane. The reaction mixture is stirred at room temperature for 4 hours, diluted with 100 ml of dichloromethane, washed two times with 100 ml of water, dried over magnesium sulfate and filtered. The solvent is carefully distilled off from the filtrate using water pump vacuum.

5.3 g (88.7% of theory) of 2-mercapto-6-trifluoromethyl-benzenesulfonamide of melting point 155° C. are obtained.

Example (II-3)

Step 1

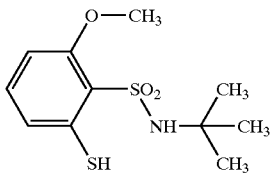

Under argon, 108 g (0.444 mol) of N-tert-butyl-2-methoxy-benzenesulfonamide are dissolved in 759 ml of (anhydrous)tetrahydrofuran, cooled to −10° C. and treated with 678 ml (1.11 mol) of 15% strength n-butyllithium solution in hexane. After the solution has been stirred for 3 hours at from 0° C. to −5° C., 23.4 g (0.73 mol) of sulfur are added, and the mixture is stirred at room temperature (about 20° C.) for a further 20 hours. While cooling to about 20° C., the reaction mixture is then adjusted to pH 1 using 2N hydrochloric acid. The solid precipitate is isolated by filtration under suction, washed with water and dried at 50° C. using water pump vacuum.

72 g (59% of theory) of N-tert-butyl-2-methoxy-6-mercapto-benzenesulfonamide of melting point 210° C. are obtained.

The filtrate is admixed with 1 liter of water and 1.5 liters of dichloromethane, and the organic phase is separated off, washed with water, dried over magnesium sulfate and freed from the solvent using water pump vacuum. A further 35.5 g (29% of theory) of N-tert-butyl-2-methoxy-6-mercapto-benzenesulfonamide are obtained.

Step 2

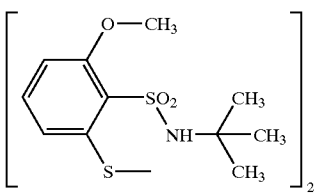

70 g (0.255 mol) of N-tert-butyl-2-methoxy-6-mercapto-benzenesulfonamide are suspended in 180 ml of dimethyl sulfoxide and heated to 90° C. for 22 hours. After cooling, the suspension is poured into about 1 liter of water. The solid precipitate is isolated by filtration under suction, washed with water and dried at 60° C. using water pump vacuum.

67.1 g (98% of theory) of bis-(2-tert-butylsulfamoyl-3-methoxy-phenyl)disulfide of melting point 275° C. are obtained.

Step 3

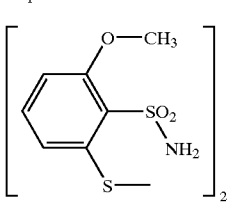

At room temperature (about 20° C.), 71 ml (0.93 mol) of trifluoroacetic acid are added dropwise to a suspension of 20.4 g (0.037 mol) of bis-(2-tert-butylsulfamoyl-3-methoxy-phenyl)disulfide in 70 ml of dichloromethane. The reaction mixture is stirred for about 23 hours at room temperature, filtered off under suction, washed with dichloromethane and dried at 60° C. under reduced pressure.

16.0 g (81% of theory) of bis-(3-methoxy-2-sulfamoyl-phenyl)disulfide of melting point 263° C. are obtained.

Step 4

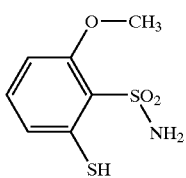

Under an atmosphere of nitrogen, 12.7 g (0.334 mol) of solid sodium borohydride are added a little at a time to a suspension of 19.2 g (0.044 mol) of bis-(3-methoxy-2-sulfamoyl-phenyl)disulfide in 180 ml of methanol. After the addition has ended, the reaction mixture is stirred for 24 hours at room temperature (about 20° C.) and admixed dropwise with about 100 ml of 1N hydrochloric acid. The major part of the methanol is removed using water pump vacuum, the solid residue is stirred with 0.5N hydrochloric acid, filtered off under suction and dried at 60° C. under reduced pressure.

13.8 g (72% of theory) of 2-methoxy-6-mercapto-benzenesulfonamide of melting point 166° C. are obtained.

Step 5

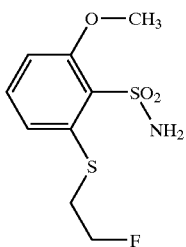

A solution of 7.5 g (34 mmol) of 2-methoxy-6-mercapto-benzenesulfonamide in 70 ml of (anhydrous)acetonitrile is treated with 9.45 g (68.5 mmol) of (anhydrous)potassium carbonate, and the mixture is stirred at room temperature (about 20° C.) for 2 hours. 4.93 g (37.7 mmol) of 1-bromo-2-fluoro-ethane are then added dropwise, and stirring is continued at room temperature for a further 24 hours. The reaction mixture is diluted with 150 ml of dichloromethane, washed with 1N hydrochloric acid, dried over magnesium sulfate and filtered. The solvent is carefully distilled off from the filtrate using water pump vacuum.

8.6 g (95% of theory) of 2-(2-fluoro-ethylthio)-6-methoxy-benzenesulfonamide of melting point 127° C. are obtained.

Example (II-4)

Step 1

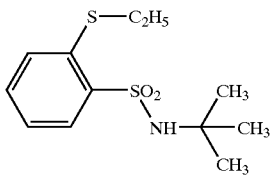

Under an atmosphere of argon, 30 g (0.14 mol) of N-tert-butyl-benzenesulfonamide are dissolved in 400 ml of (anhydrous)tetrahydrofuran, cooled to −5° C. and treated with 210 ml (0.35 mol) of 15% strength n-butyllithium solution in hexane. After the solution has been stirred for 3 hours at from 0° C. to −5° C., 4.9 g (0.153 mol) of sulfur are added, and the mixture is stirred for a further 3 hours at room temperature (about 20° C.). The reaction mixture is then treated with 24.2 g (0.155 mol) of iodoethane, stirred at room temperature for 24 hours and then admixed with 800 ml of dichloromethane. The solution is washed with 1N hydrochloric acid, dried over magnesium sulfate and concentrated using water pump vacuum. The crude product obtained as a residue is stirred with petroleum ether, filtered off under suction and dried at 40° C. under reduced pressure.

34.1 g (89% of theory) of N-tert-butyl-2-ethylthio-benzenesulfonamide of melting point 88° C. are obtained.

Step 2

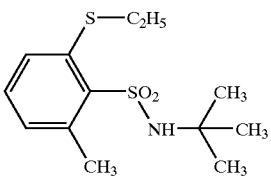

Under an atmosphere of nitrogen, 25 g (0.092 mol) of N-tert-butyl-2-ethylthio-benzenesulfonamide are dissolved in 200 ml of (anhydrous)tetrahydrofuran, cooled to −10° C. and treated with 140 ml (0.23 mol) of 15% strength n-butyllithium solution in hexane. After the solution has been stirred for 3 hours at from −10° C. to −15° C., the reaction mixture is treated with 15.6 g (0.11 mol) of iodomethane. The solution is stirred for a further 2 hours at from −15° C. to −20° C., and the temperature is then allowed to increase slowly to room temperature (about 20° C.). After 24 hours, the solution is mixed with 800 ml of dichloromethane, washed with 2N hydrochloric acid, dried over magnesium sulfate and concentrated using water pump vacuum. The crude product obtained as a residue is stirred with petroleum ether, filtered off under suction and dried at 40° C. under reduced pressure.

20.1 g (76.5% of theory) of N-tert-butyl-2-ethylthio-6-methyl-benzenesulfonamide of melting point 94° C. are obtained.

Similarly to Examples (II-1) to (II-4), it is also possible to prepare for example the compounds of the formula (II) listed in Table 2 below.

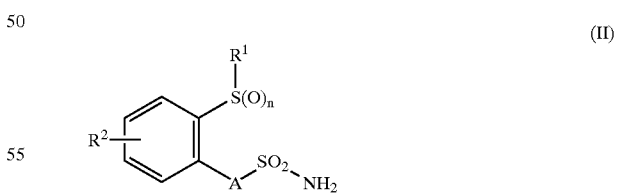

TABLE 2

Examples of the compounds of the formula (II)

| Ex. No. | n | A | R¹ | (Position-) R² | Melting point (° C.) |
|---|---|---|---|---|---|
| II-5 | 0 | — | CH₃ | (6-)C₂H₅ | |
| II-6 | 0 | — | C₂H₅ | (6-)OCH₃ | 154 |

TABLE 2-continued

Examples of the compounds of the formula (II)

| Ex. No. | n | A | R¹ | (Position-) R² | Melting point (° C.) |
|---|---|---|---|---|---|
| II-7 | 0 | — | $C_2H_5$ | (6-)F | 132 |
| II-8 | 0 | — | $C_2H_5$ | (6-)Cl | 124 |
| II-9 | 0 | — | $C_2H_5$ | (6-)$CF_3$ | 120 |
| II-10 | 1 | — | $C_2H_5$ | (6-)$CF_3$ | 112 |
| II-11 | 2 | — | $C_2H_5$ | (6-)$CF_3$ | 193 |
| II-12 | 0 | — | i-$C_3H_7$ | (6-)$OCH_3$ | 128 |
| II-13 | 0 | — | i-$C_3H_7$ | (6-)Cl | 83 |
| II-14 | 0 | — | $CH_3$ | (6-)Cl | 127 |
| II-15 | 0 | — | $CH_3$ | (6-)$OCH_3$ | 155 |
| II-16 | 0 | — | $CH_3$ | (6-)$OCF_3$ | 160 |
| II-17 | 0 | — | i-$C_3H_7$ | (6-)$OCF_3$ | 135 |
| II-18 | 0 | — | i-$C_3H_7$ | (6-)$CH_3$ | 87 |
| II-19 | 0 | — | i-$C_3H_7$ | (6-)$C_2H_5$ | 146 |
| II-20 | 0 | — | i-$C_3H_7$ | (6-)$SCH_3$ | 129 |
| II-21 | 0 | — | $C_2H_5$ | (6-)$SC_2H_5$ | 105 |
| II-22 | 0 | — | $C_2H_4OCOCF_3$ | (6-)$OCH_3$ | 135 |
| II-23 | 0 | — | $CH_3$ | (6-)$SCH_3$ | 120 |
| II-24 | 0 | — | $C_2H_5$ | (6-)$CH_3$ | 192 |
| II-25 | 0 | — | $CH_3$ | (6-)$CH_3$ | 164 |
| II-26 | 0 | — | $CH_3$ | (6-)$CF_3$ | 130 |
| II-27 | 0 | — | H | (6-)$OCF_3$ | 146 |
| II-28 | 0 | — | $C_2H_4F$ | (6-)$OCF_3$ | |
| II-29 | 0 | — | $C_2H_4F$ | (6-)$CF_3$ | 131 |
| II-30 | 0 | — | i-$C_3H_7$ | (6-)$CF_3$ | 138 |
| II-31 | 0 | — | $CH_2C\equiv H$ | (6-)$OCF_3$ | 105 |
| II-32 | 0 | — | $CF_3$ | (6-)$OCF_3$ | 85 |
| II-33 | 0 | — | $C_2H_3F_2$ | (6-)$CF_3$ | 110 |
| II-34 | 0 | — | $C_3H_6F$ | (6-)$CF_3$ | 112 |
| II-35 | 0 | — | $CH_2F$ | (6-)$OCF_3$ | 163 |
| II-36 | 0 | — | $CF_3$ | (6-)$CF_3$ | |
| II-37 | 0 | — | $CF_3$ | (6-)$OCH_3$ | |

USE EXAMPLES

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of the active compound in such a way as to apply the particular amounts of active compound desired per unit area The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

| | |
|---|---|
| 0% = | no action (like untreated control) |
| 100% = | total destruction |

In this test, a very strong activity against weeds (cf. Tables A-1 to A-5) is shown, for example, by the compounds of Preparation Examples 1, 6, 7, 8, 11, 13, 14, 20, 21, 22, 24, 25, 30, 32, 33, 34, 35, 40, 41, 57, 59, 60, 61, 62 and 63, combined with good tolerance of some compounds by crop plants, such as for example maize, wheat, cotton and soya beans.

"ai."=active ingredient

TABLE A-1

Pre-emergence test/greenhouse

| Active compound as per Preparation Ex. No. | g ai./ha | Maize | Alopecurus | Lolium | Sorghum | Amaranthus | Chenopodium | Matricaria | Solanum |
|---|---|---|---|---|---|---|---|---|---|
| 6 | 125 | 0 | 100 | 100 | 80 | 100 | 100 | 100 | 100 |
| 7 | 125 | 0 | 100 | 100 | 90 | 100 | 100 | 70 | 100 |
| 8 | 125 | 0 | 100 | 80 | — | 100 | 100 | — | 60 |
| 11 | 125 | 10 | 100 | 90 | 100 | 100 | 100 | 100 | 100 |
| 13 | 125 | 0 | 90 | 90 | 100 | 100 | 100 | 100 | 100 |
| 14 | 125 | 0 | 100 | — | 90 | 70 | 100 | 100 | 100 |
| 1 | 125 | 0 | 95 | 70 | 90 | 90 | 60 | 70 | 100 |
| 20 | 60 | 0 | 100 | 95 | 100 | 100 | 100 | 100 | 100 |
| 21 | 60 | 20 | 100 | 100 | 100 | 100 | 100 | 90 | 100 |
| 22 | 125 | 30 | 100 | 100 | 80 | 100 | — | 60 | 100 |
| 30 | 60 | 0 | 100 | 100 | 95 | 95 | 90 | 95 | 95 |
| 32 | 30 | 5 | 90 | 100 | 90 | 100 | 100 | 90 | 95 |
| 33 | 125 | 10 | 100 | 100 | 100 | 100 | 100 | 100 | 100 |
| 34 | 60 | 20 | 100 | 80 | 90 | 90 | 90 | — | 95 |
| 57 | 125 | — | 100 | 100 | 100 | 100 | 100 | — | — |
| 59 | 125 | — | 100 | 100 | 100 | 100 | 100 | 100 | 100 |
| 62 | 60 | 10 | 100 | 100 | 90 | 100 | 100 | — | 100 |
| 63 | 60 | 0 | 100 | 70 | 100 | 100 | 100 | — | 100 |

TABLE A-2

Pre-emergence/greenhouse

| Active compound as per Preparation Ex. No. | g ai./ha | Wheat | Alopecurus | Lolium | Sorghum | Amaranthus | Chenopodium | Solanum | Veronica |
|---|---|---|---|---|---|---|---|---|---|
| 35 | 60 | 10 | 100 | 95 | 90 | 100 | 100 | 95 | 100 |

TABLE A-3

Pre-emergence/greenhouse

| Active compound as per Preparation Ex. No. | g ai./ha | Maize | Cotton | Alopecurus | Sorghum | Amaranthus | Chenopodium | Matricaria | Viola |
|---|---|---|---|---|---|---|---|---|---|
| 24 | 125 | 0 | 0 | 95 | 70 | 100 | 100 | 70 | 100 |

TABLE A-4

Pre-emergence/greenhouse

| Active compound as per Preparation Ex. No. | g ai./ha | Maize | Soya beans | Alopecurus | Lolium | Sorghum | Amaranthus | Chenopodium | Matricaria | Solanum |
|---|---|---|---|---|---|---|---|---|---|---|
| 25 | 125 | 0 | 20 | 100 | 70 | 80 | 95 | 100 | 95 | 100 |
| 40 | 125 | 5 | 20 | 100 | 95 | 100 | 100 | 100 | 100 | 100 |
| 41 | 125 | 10 | 20 | 100 | 80 | 90 | 100 | 100 | 100 | 100 |

TABLE A-5

Pre-emergence/greenhouse

| Active compound as per Preparation Ex. No. | g ai./ha | Wheat | Cotton | Alopecurus | Bromus | Echinochloa | Amaranthus | Chenopodium | Veronica |
|---|---|---|---|---|---|---|---|---|---|
| 60 | 125 | 0 | 20 | 90 | 95 | 100 | 100 | 100 | 100 |
| 61 | 60 | 30 | 0 | 95 | 100 | 100 | 100 | 100 | 80 |

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

| | |
|---|---|
| 0% = | no action (like untreated control) |
| 100% = | total destruction |

In this test, a very strong activity against weeds (cf. Tables B-1 to B-4) is shown, for example, by the compounds of Preparation Examples 6, 7, 11, 13, 20, 21, 22, 24, 30, 34, 39, 40, 43, 44, 46, 48, 49, 50, 51, 52, 53, 55, 56 and 59, combined with good tolerance of some compounds by crops, such as for example wheat; "ai."=active ingredient.

TABLE B-1

Post-emergence test/greenhouse

| Active compound as per Preparation Ex. No. | g ai./ha | Wheat | Alopecurus | Lolium | Sorghum | Ipomoea | Solanum | Stellaria | Xanthium |
|---|---|---|---|---|---|---|---|---|---|
| 20 | 60 | 20 | 95 | 90 | 100 | 95 | 100 | 100 | 95 |
| 21 | 60 | — | 100 | 95 | 100 | 90 | 100 | 100 | — |
| 22 | 60 | — | 90 | 90 | 95 | 80 | 80 | 90 | — |
| 24 | 60 | 15 | 90 | 60 | 90 | 90 | 95 | 95 | — |
| 30 | 125 | — | 95 | 90 | 100 | 90 | 100 | 100 | 100 |
| 34 | 60 | 20 | 90 | 70 | 100 | 80 | 95 | 80 | 95 |
| 6 | 60 | 5 | 60 | 50 | 70 | 90 | 95 | 95 | 95 |
| 7 | 60 | 10 | 95 | 95 | 95 | 95 | 95 | 100 | — |
| 52 | 60 | — | 90 | 60 | 100 | 90 | 95 | 95 | 95 |

TABLE B-2

Post-emergence/greenhouse

| Active compound as per Preparation Ex. No. | g ai./ha | Wheat | Sorghum | Ipomoea | Solanum | Stellaria | Xanthium |
|---|---|---|---|---|---|---|---|
| 11 | 60 | 0 | — | 90 | 70 | 90 | 90 |
| 13 | 60 | 0 | 80 | 90 | 95 | 95 | — |
| 39 | 60 | 20 | 80 | 80 | 95 | 90 | 95 |
| 40 | 60 | 20 | 80 | 90 | 95 | 95 | 100 |
| 43 | 60 | 20 | 70 | 95 | 95 | 90 | 100 |
| 44 | 60 | 10 | 70 | 95 | 95 | 80 | 100 |
| 46 | 60 | — | 70 | 9S | 95 | 95 | 100 |
| 48 | 60 | 5 | 100 | 90 | 90 | 60 | 95 |
| 49 | 60 | 20 | 90 | 90 | 90 | 70 | 95 |
| 53 | 125 | 20 | 95 | 95 | 59 | 90 | 100 |

TABLE B-3

Post-emergence/greenhouse

| Active compound as per Preparation Ex. No. | g ai./ ha | Wheat | Amaranthus | Matricaria | Solanum | Xanthium |
|---|---|---|---|---|---|---|
| 55 | 60 | 20 | 95 | 95 | 90 | 100 |
| 56 | 125 | 10 | 100 | 100 | 100 | 100 |
| 51 | 125 | 20 | 95 | 95 | 95 | 95 |

TABLE B-4

Post-emergence/greenhouse

| Active compound as per Preparation Ex. No. | g ai./ ha | Echinochloa | Sorghum | Amaranthus | Solanum | Xanthium |
|---|---|---|---|---|---|---|
| 59 | 60 | 100 | 100 | 100 | 90 | 95 |
| 49 | 60 | — | 90 | 95 | 90 | 95 |
| 50 | 60 | 80 | 95 | 95 | 95 | 95 |

We claim:

1. A sulfonylamino(thio)carbonyl of the formula (I)

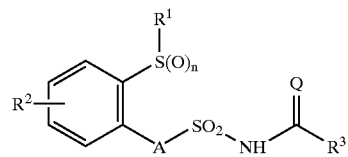

(I)

wherein n represents the number 0,

A represents a single bond,

Q represents oxygen, $R^1$ represents optionally fluoro-, chloro-, or bromo substituted alkyl having in each case up to 6 carbon atoms, $R^2$ represents fluoro, chloro or bromo or represents optionally fluoro-, chloro-, or bromo substituted alkyl, alkoxy, or alkylthio, having in each case up to 6 carbon atoms, and $R^3$ represents an optionally substituted heterocyclyl of the formula below,

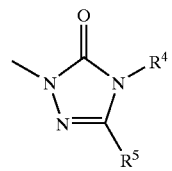

wherein
R[4] represents hydrogen, hydroxyl, amino or cyano, or represents $C_2$–$C_{10}$-alkylideneamino, or represents optionally fluoro-, chloro-, bromo-, cyano-, $C_1$–$C_4$-alkoxy-, $C_1$–$C_4$-alkyl-carbonyl- or $C_1$–$C_4$-alkoxy-carbonyl-substituted $C_1$–$C^6$-alkyl, or represents optionally fluoro-, chloro- and/or bromo-substituted $C_2$–$C_6$-alkenyl or $C_2$–$C_6$-alkynyl, or represents optionally fluoro-, chloro-, bromo-, cyano-, $C_1$–$C_4$-alkoxy- or $C_1$–$C_4$-alkoxy-carbonyl-substituted $C_1$–$C_6$-alkoxy, $C_1$–$C_6$-alkylamino or $C_1$–$C_6$-alkyl-carbonylamino, or represents $C_3$–$C_6$-alkenyloxy, or represents di-($C_1$–$C_4$-alkyl)-amino, or represents optionally fluoro-, chloro-, bromo-, cyano- and/or $C_1$–$C_4$-alkyl-substituted $C_3$–$C_6$-cycloalkyl, $C_3$–$C_6$-cycloalkylamino or $C_3$–$C_6$-cycloalkyl-$C_1$–$C_4$-alkyl, or represents optionally fluoro-, chloro-, bromo-, cyano-, nitro-, $C_1$–$C_4$-alkyl-, trifluoromethyl- and/or $C_1$–$C_4$-alkoxy-substituted phenyl or phenyl-$C_1$–$C_4$-alkyl, R[5] represents hydrogen, hydroxyl, mercapto, amino, cyano, fluoro, chloro, bromo or iodo, or represents optionally fluoro-, chloro-, bromo-, cyano-, $C_1$–$C_4$-alkoxy-, $C_1$–$C_4$-alkyl-carbonyl- or $C_1$–$C_4$-alkoxy-carbonyl-substituted $C_1$–$C_6$-alkyl, or represents optionally fluoro-, chloro- and/or bromo-substituted $C_2$–$C_6$-alkenyl or $C_2$–$C_6$-alkynyl, or represents optionally fluoro-, chloro-, cyano-, $C_1$–$C_4$-alkoxy- or $C_1$–$C_4$-alkoxy-carbonyl-substituted $C_1$–$C_6$-alkoxy, $C_1$–$C_6$-alkylthio, $C_1$–$C_6$-alkylamino or $C_1$–$C_6$-alkylcarbonylamino, or represents $C_3$–$C_6$-alkenyloxy, $C_3$–$C_6$-alkynyloxy, $C_3$–$C_6$-alkenylthio, $C_3$–$C_6$-alkynylthio, $C_3$–$C_6$-alkenylamino or $C_3$–$C_6$-alkynylamino, or represents di-($C_1$–$C_4$-alkyl)-amino, or represents optionally methyl- and/or ethyl-substituted aziridino, pyrrolidino, or represents optionally fluoro-, chloro-, bromo-, cyano- and/or $C_1$–$C_4$-alkyl-substituted $C_3$–$C_6$-cycloalkyl, $C_5$–$C_6$-cycloalkenyl, $C_3$–$C_6$-cycloalkyloxy, $C_3$–$C_6$-cycloalkylthio, $C_3$–$C_6$-cycloalkylamino, $C_3$–$C_6$-cycloalkyl-$C_1$–$C_4$-alkyl, $C_3$–$C_6$-cycloalkyl-$C_1$–$C_4$-alkoxy, $C_3$–$C_6$-cycloalkyl-$C_1$–$C_4$-alkylthio or $C_3$–$C_6$-cycloalkyl-$C_1$–$C_4$-alkylamino, or represents optionally fluoro-, chloro-, bromo-, cyano-, nitro-, $C_1$–$C_4$-alkyl-, trifluoromethyl-, $C_1$–$C_4$-alkoxy- and/ or $C_1$–$C_4$-alkoxy-carbonyl-substituted phenyl, phenyl-$C_1$–$C_4$-alkyl, phenoxy, phenyl-$C_1$–$C_4$-alkoxy, phenylthio, phenyl-$C_1$–$C_4$-alkylthio, phenylamino or phenyl-$C_1$–$C_4$-alkylamino, or R[4] and R[5] together represent optionally branched alkanediyl having 3 to 11 carbon atoms, and salts thereof.

2. The sulfonylamino(thio)carbonyl of claim 1, wherein n represents the number 0, A represents a single bond, Q represents oxygen, R[1] represents optionally fluoro-, chloro-, or bromo-, substituted methyl, ethyl, n- or i-propyl, n-, i- or s-butyl, R[2] represents fluoro, chloro or bromo, or represents optionally fluoro-, or chloro-, substituted methyl, ethyl, n- or i-propyl, n-, i- or s-butyl, methoxy, ethoxy, n- or i-propoxy, n-, i- or s-butoxy, methylthio, ethylthio, n- or i-propylthio, n-, i-, s- or t-butylthio, and R[3] represents an optionally substituted heterocyclyl of the formula below:

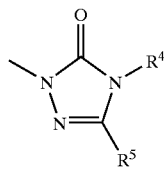

wherein
R[4] represents hydrogen, hydroxyl or amino, or represents $C_3$–$C_8$-alkylideneamino, or represents optionally fluoro-, chloro-, cyano-, methoxy- or ethoxy-substituted methyl, ethyl, n- or i-propyl, n-, i-, s- or t-butyl, or represents optionally fluoro-, chloro- or bromo-substituted propenyl, butenyl, propynyl or butynyl, or represents optionally fluoro-, chloro-, cyano-, methoxy- or ethoxy-substituted methoxy, ethoxy, n- or i-propoxy, n-, i-, s- or t-butoxy, methylamino, ethylamino, n- or i-propylamino, n-, i-, s- or t-butylamino, or represents propenyloxy or butenyloxy, or represents dimethylamino or diethylamino, or represents optionally fluoro-, chloro-, methyl- and/or ethyl-substituted cyclopropyl, cyclobutyl, cyclopentyl, cyclohexyl, cyclopropylamino, cyclobutylamino, cyclopentylamino, cyclohexylamino, cyclopropylmethyl, cyclobutylmethyl, cyclopentylmethyl or cyclohexylmethyl, or represents optionally fluoro-, chloro-, methyl-, trifluoromethyl- and/or methoxy-substituted phenyl or benzyl, R[5] represents hydrogen, hydroxyl, mercapto, amino, fluoro, chloro or bromo, or represents optionally fluoro-, chloro-, cyano-, methoxy- or ethoxy-substituted methyl, ethyl, n- or i-propyl, n-, i-, s- or t-butyl, or represents optionally fluoro-, chloro- or bromo-substituted ethenyl, propenyl, butenyl, propynyl or butynyl, or represents optionally fluoro-, chloro-, cyano-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, or represents propenyloxy, butenyloxy, propynyloxy, butynyloxy, propenylthio, propadienylthio, butenylthio, propynylthio, butynylthio, propenylamino, butenylamino, propynylamino or butynyl amino, or represents dimethylamino, diethylamino or dipropylamino, or represents optionally fluoro-, chloro-, methyl- and/or ethyl-substituted cyclopropyl, cyclobutyl, cyclopentyl, cyclohexyl, cyclopentenyl, cyclohexenyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl, cyclohexylmethyl, cyclopropylmethoxy, cyclobutylmethoxy, cyclopentylmethoxy, cyclohexylmethoxy, cyclopropylmethylthio, cyclobutylmethylthio, cyclopentylmethylthio, cyclohexylmethylthio, cyclopropylmethylamino, cyclobutylmethylamino, cyclopentylmethylamino or cyclohexylmethylamino, or represents optionally fluoro-, chloro-, methyl-, trifluoromethyl-, methoxy- and/or methoxycarbonyl-substituted phenyl, benzyl, phenoxy, benzyloxy, phenylthio, benzylthio, phenylamino or benzylamino, or $R^4$ and $R^5$ together represent optionally branched alkanediyl having 3 to 11 carbon atoms.

3. The sulfonylamino(thio)carbonyl of claim 1, wherein n represents the number 0, A represents a single bond, Q represents oxygen, $R^1$ represents optionally fluoro- and/or chloro-substituted methyl, ethyl, n- or i-propyl, n-, i-, s- or t-butyl, $R^2$ represents fluoro, chloro or bromo, or represents optionally fluoro-, and/or chloro-substituted methyl, ethyl, methoxy, ethoxy, methylthio or ethylthio—in each case in position 6-, and $R^3$ represents an optionally substituted triazolinyl of the formula below, wherein

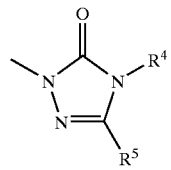

$R^4$ represents optionally fluoro-, chloro-, cyano-, methoxy- or ethoxy-substituted methyl, ethyl, n- or i-propyl, or represents propenyl or propynyl, or represents methoxy, ethoxy, n- or i-propoxy, or represents cyclopropyl, and $R^5$ represents hydrogen, chloro or bromo, or represents optionally fluoro-, chloro-, cyano-, methoxy- or ethoxy-substituted methyl, ethyl, n- or i-propyl, or represents optionally fluoro- and/or chloro-substituted propenyl or propynyl, or represents optionally fluoro-, chloro-, cyano-, methoxy- or ethoxy-substituted methoxy, ethoxy, n- or i-propoxy, methylthio, ethylthio, n- or i-propylthio, or represents propenyloxy or cyclopropyl.

4. A process for preparing the sulfonylamino(thio)carbonyl of claim 1 comprising reacting an aminosulfonyl of the formula (II)

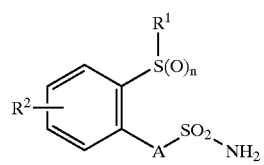  (II)

wherein
n, A, $R^1$ and $R^2$ are as defined in claim 2 with a (thio)carboxylic acid of the formula (III)

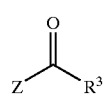  (III)

wherein
Q and $R^3$ are as defined in claim 2 and
Z represents halogen, alkoxy, aryloxy or arylalkoxy, or reacting a sulfonyl iso(thio)cyanate of the formula (IV)

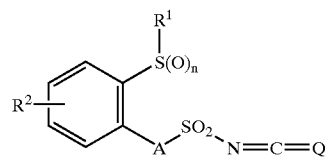  (IV)

wherein
n, A, Q, $R^1$ and $R^2$ are as defined above with a heterocycle of the formula (V)

H—$R^3$  (V)

wherein
$R^3$ is as defined above, or reacting a chlorosulfonyl of the formula (VI)

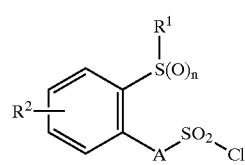  (VI)

wherein
n, A, $R^1$ and $R^2$ are as defined above with a heterocycle of the formula (V)

H—$R^3$  (V)

wherein
$R^3$ is as defined above and
a metal (thio)cyanate of the formula (VII)

MQCN  (VII)

wherein
Q is as defined above, or reacting a chlorosulfonyl of the formula (VI)

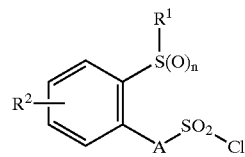  (VI)

wherein
n, A, $R^1$ and $R^2$ are as defined above with a (thio) carboxamide of the formula (VIII)

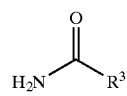  (VIII)

wherein
Q and $R^3$ are as defined above, or reacting a sulfonylamino(thio)carbonyl of the formula (IX)

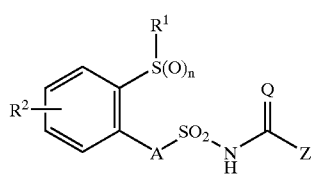

wherein
n, A, Q, R¹ and R² are as defined above and
Z represents halogen, alkoxy, aryloxy or arylalkoxy,
with a heterocycle of the formula (V)

 (V)

wherein
R³ is as defined above, or
reacting a heterocycle of the formula (V)

 (V)

wherein
R³ is as defined above,
with chlorosulfonyl iso(thio)cyanate, optionally in the presence of a diluent, and reacting the adducts formed in situ with a benzene of the formula (X)

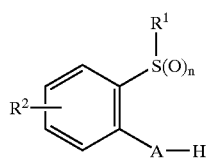

wherein
n, A, R¹ and R² are as defined above, and collecting the reaction product.

5. A herbicidal composition comprising at least one compound of claim 1 and at least one of extenders and surfactants.

6. A method for controlling at least one weed comprising applying at least one sulfonylamino(thio)carbonyl of claim 1 to the weed and/or its habitat.

7. A method for preparing herbicidal composition comprising mixing at least one sulfonylamino(thio)carbonyl of claim 1 with at least one of extenders and surface-active agents.

8. The sulfonylamino(thio)carbonyl of claim 1, wherein

A represents a single bond;
Q represents oxygen;
$R^1$ represents $C_2H_5$;
$R^2$ represents (6-)$OCH_3$ and
$R^3$ represents

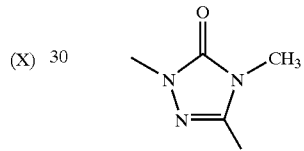

\* \* \* \* \*